US008328794B2

(12) United States Patent
Altshuler et al.

(10) Patent No.: US 8,328,794 B2
(45) Date of Patent: Dec. 11, 2012

(54) SYSTEM FOR ELECTROMAGNETIC RADIATION DERMATOLOGY AND HEAD FOR USE THEREWITH

(75) Inventors: Gregory B. Altshuler, Lincoln, MA (US); Henry H. Zenzie, Dover, MA (US)

(73) Assignee: Palomar Medical Technologies, Inc., Burlington, MA (US)

(*) Notice: Subject to any disclaimer, the term of this patent is extended or adjusted under 35 U.S.C. 154(b) by 836 days.

(21) Appl. No.: 12/234,892

(22) Filed: Sep. 22, 2008

(65) Prior Publication Data
US 2009/0137995 A1 May 28, 2009

Related U.S. Application Data

(63) Continuation of application No. 11/093,693, filed on Mar. 30, 2005, now Pat. No. 7,431,719, which is a continuation of application No. 10/245,825, filed on Sep. 17, 2002, now Pat. No. 6,878,144, which is a continuation of application No. 09/268,433, filed on Mar. 12, 1999, now Pat. No. 6,508,813, which is a continuation-in-part of application No. 08/759,036, filed on Dec. 2, 1996, now Pat. No. 6,015,404, and a continuation-in-part of application No. 08/759,136, filed on Dec. 2, 1996, now abandoned, and a continuation-in-part of application No. 09/078,055, filed on May 13, 1998, now Pat. No. 6,273,884, application No. 12/234,892, which is a continuation-in-part of application No. 09/473,910, filed on Dec. 28, 1999, now Pat. No. 6,517,532, and a continuation-in-part of application No. 09/078,055, filed on May 13, 1998, now Pat. No. 6,273,884, application No. 12/234,892, which is a continuation-in-part of application No. 09/634,981, filed on Aug. 9, 2000, now Pat. No. 6,511,475, which is a continuation of application No. 09/078,055, filed on May 13, 1998, now Pat. No. 6,273,884.

(60) Provisional application No. 60/115,447, filed on Jan. 8, 1999, provisional application No. 60/077,794, filed on Mar. 12, 1998, provisional application No. 60/046,542, filed on May 15, 1997, provisional application No. 60/077,726, filed on Mar. 12, 1998, provisional application No. 60/164,492, filed on Nov. 9, 1999.

(51) Int. Cl.
 *A61B 18/18* (2006.01)
(52) U.S. Cl. .............................................. 606/9; 606/13
(58) Field of Classification Search .................. 606/9, 2, 606/13–19; 607/88–94; 600/473–476
 See application file for complete search history.

(56) References Cited

U.S. PATENT DOCUMENTS 853,033 A    5/1907   Roberts
(Continued)

FOREIGN PATENT DOCUMENTS

AT          400305        4/1995
(Continued)

OTHER PUBLICATIONS

Ohshiro et al., "The Ruby and Argon Lasers in the Treatment of the Naevi," Annals Academy of Medicine, Apr. 1983, vol. 12, No. 2, pp. 388-395.
(Continued)

*Primary Examiner* — Kevin C Sirmons
*Assistant Examiner* — Phillip Gray
(74) *Attorney, Agent, or Firm* — Thomas J. Engellener; Reza Mollaaghababa; Pepper Hamilton LLP

(57) ABSTRACT

A system for treating a selected dermatological problem and a head. The head may include an optical waveguide having a first end to which EM radiation appropriate for treating the condition is applied. The waveguide also has a skin-contacting second end opposite the first end, which is in contact with the skin, and has a reflection aperture which is substantially as great as the radiation back-scatter aperture from the patient's skin. The portion of the back-scattered radiation entering the waveguide is substantially internally reflected therein, with a reflector being provided. The reflector may be angle dependent so as to more strongly reflect back scattered light more perpendicular to the skin surface than back scattered radiation more parallel to the skin surface. The head may also have a mechanism for forming a reflecting chamber under the waveguide and drawing a fold of skin therein.

21 Claims, 10 Drawing Sheets

U.S. PATENT DOCUMENTS

| | | |
|---|---|---|
| 1,590,283 A | 6/1926 | Catlin |
| 1,706,161 A | 3/1929 | Hollnagen |
| 2,472,385 A | 6/1949 | Rollman |
| 2,669,771 A | 2/1954 | Burge et al. |
| 3,261,978 A | 7/1966 | Brenman |
| 3,327,712 A | 6/1967 | Kaufmann |
| 3,486,070 A | 12/1969 | Engel |
| 3,527,932 A | 9/1970 | Thomas |
| 3,538,919 A | 11/1970 | Meyer |
| 3,597,652 A | 8/1971 | Gates, Jr. |
| 3,622,743 | 11/1971 | Muncheryan |
| 3,653,778 A | 4/1972 | Freiling |
| 3,667,454 A | 6/1972 | Prince |
| 3,693,623 A | 9/1972 | Harte et al. |
| 3,793,723 A | 2/1974 | Kuris et al. |
| 3,818,914 A | 6/1974 | Bender |
| 3,834,391 A | 9/1974 | Block |
| 3,846,811 A | 11/1974 | Nakamura et al. |
| 3,857,015 A | 12/1974 | Clark et al. |
| 3,890,537 A | 6/1975 | Park et al. |
| 3,900,034 A | 8/1975 | Katz et al. |
| 3,909,649 A | 9/1975 | Arsena |
| 3,939,560 A | 2/1976 | Lyall |
| 3,977,083 A | 8/1976 | Leslie et al. |
| 4,047,106 A | 9/1977 | Robinson |
| 4,213,462 A | 7/1980 | Sato |
| 4,233,493 A | 11/1980 | Nath et al. |
| 4,269,067 A | 5/1981 | Tynan et al. |
| 4,273,109 A | 6/1981 | Enderby |
| 4,275,335 A | 6/1981 | Ishida et al. |
| 4,298,005 A | 11/1981 | Mutzhas |
| 4,316,467 A | 2/1982 | Muckerheide |
| 4,333,197 A | 6/1982 | Kuris |
| 4,335,726 A | 6/1982 | Kolstedt |
| 4,388,924 A | 6/1983 | Weissman et al. |
| 4,409,479 A | 10/1983 | Sprague et al. |
| 4,452,081 A | 6/1984 | Seppi |
| 4,456,872 A | 6/1984 | Froeschle |
| 4,461,294 A | 7/1984 | Baron |
| 4,504,727 A | 3/1985 | Melcher et al. |
| 4,512,197 A | 4/1985 | von Gutfeld et al. |
| 4,524,289 A | 6/1985 | Hammond et al. |
| 4,539,987 A | 9/1985 | Nath et al. |
| 4,553,546 A | 11/1985 | Javelle |
| 4,561,440 A | 12/1985 | Kubo et al. |
| 4,566,271 A | 1/1986 | French et al. |
| 4,591,762 A | 5/1986 | Nakamura |
| 4,601,753 A | 7/1986 | Soileau et al. |
| 4,608,978 A | 9/1986 | Rohr |
| 4,608,979 A | 9/1986 | Breidenthal et al. |
| 4,617,926 A | 10/1986 | Sutton |
| 4,623,929 A | 11/1986 | Johnson et al. |
| 4,653,495 A | 3/1987 | Nanaumi |
| 4,677,347 A | 6/1987 | Nakamura et al. |
| 4,695,697 A | 9/1987 | Kosa |
| 4,710,677 A | 12/1987 | Halberstadt et al. |
| 4,718,416 A | 1/1988 | Nanaumi |
| 4,733,660 A | 3/1988 | Itzkan |
| 4,736,745 A | 4/1988 | Gluckman |
| 4,745,909 A | 5/1988 | Pelton et al. |
| 4,747,660 A | 5/1988 | Nishioka et al. |
| 4,749,913 A | 6/1988 | Stuermer et al. |
| 4,775,361 A | 10/1988 | Jacques et al. |
| 4,779,173 A | 10/1988 | Carr et al. |
| 4,784,135 A | 11/1988 | Blum et al. |
| 4,799,479 A | 1/1989 | Spears |
| 4,819,669 A | 4/1989 | Politzer |
| 4,826,431 A | 5/1989 | Fujimura et al. |
| 4,832,024 A | 5/1989 | Boussignac et al. |
| 4,840,174 A | 6/1989 | Gluckman |
| 4,840,563 A | 6/1989 | Altendorf |
| 4,845,608 A | 7/1989 | Gdula |
| 4,852,549 A | 8/1989 | Mori et al. |
| 4,860,172 A | 8/1989 | Schlager et al. |
| 4,860,744 A | 8/1989 | Johnson et al. |
| 4,862,903 A | 9/1989 | Campbell |
| 4,871,479 A | 10/1989 | Bachelard et al. |
| 4,884,560 A | 12/1989 | Kuracina |
| 4,898,438 A | 2/1990 | Mori |
| 4,905,690 A | 3/1990 | Ohshiro et al. |
| 4,914,298 A | 4/1990 | Quad et al. |
| 4,917,084 A | 4/1990 | Sinofsky |
| 4,926,227 A | 5/1990 | Jensen |
| 4,928,038 A | 5/1990 | Nerone |
| 4,930,504 A | 6/1990 | Diamantopoulos et al. |
| 4,945,239 A | 7/1990 | Wist et al. |
| 4,973,848 A | 11/1990 | Kolobanov et al. |
| 4,976,308 A | 12/1990 | Faghri |
| 4,979,180 A | 12/1990 | Muncheryan |
| 4,992,256 A | 2/1991 | Skaggs et al. |
| 5,000,752 A | 3/1991 | Hoskin et al. |
| 5,030,090 A | 7/1991 | Maeda et al. |
| 5,032,178 A | 7/1991 | Cornell |
| 5,046,494 A | 9/1991 | Searfoss et al. |
| 5,050,597 A | 9/1991 | Daikuzono |
| 5,057,104 A | 10/1991 | Chess |
| 5,059,192 A | 10/1991 | Zaias |
| 5,065,515 A | 11/1991 | Iderosa |
| 5,071,417 A | 12/1991 | Sinofsky |
| 5,108,388 A | 4/1992 | Trokel |
| 5,127,395 A | 7/1992 | Bontemps |
| 5,133,102 A | 7/1992 | Sakuma et al. |
| 5,137,530 A | 8/1992 | Sand |
| 5,140,984 A | 8/1992 | Dew et al. |
| 5,159,601 A | 10/1992 | Huber |
| 5,160,194 A | 11/1992 | Feldman |
| 5,171,564 A | 12/1992 | Nathoo et al. |
| 5,178,617 A | 1/1993 | Kuizenga et al. |
| 5,182,557 A | 1/1993 | Lang |
| 5,182,857 A | 2/1993 | Simon |
| 5,192,278 A | 3/1993 | Hayes et al. |
| 5,196,004 A | 3/1993 | Sinofsky |
| 5,207,671 A | 5/1993 | Franken et al. |
| 5,222,907 A | 6/1993 | Katabuchi et al. |
| 5,225,926 A | 7/1993 | Cuomo et al. |
| 5,226,907 A | 7/1993 | Tankovich |
| 5,267,399 A | 12/1993 | Johnston |
| 5,281,211 A | 1/1994 | Parel et al. |
| 5,282,797 A | 2/1994 | Chess |
| 5,287,372 A | 2/1994 | Ortiz |
| 5,287,380 A | 2/1994 | Hsia |
| 5,293,880 A | 3/1994 | Levitt |
| 5,300,097 A | 4/1994 | Lerner et al. |
| 5,303,585 A | 4/1994 | Lichte |
| 5,304,170 A | 4/1994 | Green |
| 5,304,173 A | 4/1994 | Kittrell et al. |
| 5,306,143 A | 4/1994 | Levy |
| 5,306,274 A | 4/1994 | Long |
| 5,320,618 A | 6/1994 | Gustafsson |
| 5,334,191 A | 8/1994 | Poppas et al. |
| 5,334,193 A | 8/1994 | Nardella |
| 5,336,217 A | 8/1994 | Buys et al. |
| 5,342,358 A | 8/1994 | Daikuzono et al. |
| 5,344,418 A | 9/1994 | Ghaffari |
| 5,344,434 A | 9/1994 | Talmore |
| 5,348,551 A | 9/1994 | Spears et al. |
| 5,350,376 A | 9/1994 | Brown |
| 5,353,020 A | 10/1994 | Schurmann |
| 5,353,790 A | 10/1994 | Jacques et al. |
| 5,358,503 A | 10/1994 | Bertwell et al. |
| 5,360,426 A | 11/1994 | Muller et al. |
| 5,369,831 A | 12/1994 | Bock |
| 5,380,317 A | 1/1995 | Everett et al. |
| 5,386,427 A | 1/1995 | Zayhowski |
| 5,403,306 A | 4/1995 | Edwards et al. |
| 5,405,368 A | 4/1995 | Eckhouse |
| 5,415,654 A | 5/1995 | Daikuzono |
| 5,425,728 A | 6/1995 | Tankovich |
| 5,425,754 A | 6/1995 | Braun et al. |
| 5,445,608 A | 8/1995 | Chen et al. |
| 5,445,611 A | 8/1995 | Eppstein et al. |
| 5,454,807 A | 10/1995 | Lennox et al. |
| 5,458,140 A | 10/1995 | Eppstein et al. |
| 5,474,549 A | 12/1995 | Ortiz et al. |
| 5,486,170 A | 1/1996 | Winston et al. |
| 5,486,172 A | 1/1996 | Chess |
| 5,501,680 A | 3/1996 | Kurtz et al. |

| | | | | | | |
|---|---|---|---|---|---|---|
| 5,502,582 A | 3/1996 | Larson et al. | | 5,879,159 A | 3/1999 | Cipolla |
| 5,505,726 A | 4/1996 | Meserol | | 5,883,471 A | 3/1999 | Rodman et al. |
| 5,505,727 A | 4/1996 | Keller | | 5,885,211 A | 3/1999 | Eppstein et al. |
| 5,519,534 A | 5/1996 | Smith et al. | | 5,885,273 A | 3/1999 | Eckhouse et al. |
| 5,522,813 A | 6/1996 | Trelles | | 5,885,274 A | 3/1999 | Fullmer et al. |
| 5,527,368 A | 6/1996 | Supkis et al. | | 5,891,063 A | 4/1999 | Vigil |
| 5,531,739 A | 7/1996 | Trelles | | 5,893,828 A | 4/1999 | Uram |
| 5,531,740 A | 7/1996 | Black | | 5,895,350 A | 4/1999 | Hori |
| 5,536,168 A | 7/1996 | Bourke et al. | | 5,906,609 A | 5/1999 | Assa et al. |
| 5,549,660 A | 8/1996 | Mendes et al. | | 5,908,418 A | 6/1999 | Dority et al. |
| 5,558,667 A | 9/1996 | Yarborough et al. | | 5,913,883 A | 6/1999 | Alexander et al. |
| 5,561,881 A | 10/1996 | Klinger et al. | | 5,916,211 A | 6/1999 | Quon et al. |
| 5,571,098 A | 11/1996 | Domankevitz et al. | | 5,920,374 A | 7/1999 | Vaphiades et al. |
| 5,578,866 A | 11/1996 | DePoorter et al. | | 5,921,926 A | 7/1999 | Rolland et al. |
| 5,595,568 A | 1/1997 | Anderson et al. | | 5,928,222 A | 7/1999 | Kleinerman |
| 5,616,140 A | 4/1997 | Prescott | | 5,944,687 A | 8/1999 | Benett et al. |
| 5,620,478 A | 4/1997 | Eckhouse et al. | | 5,944,748 A | 8/1999 | Mager et al. |
| 5,626,631 A | 5/1997 | Eckhouse et al. | | 5,948,011 A | 9/1999 | Knowlton |
| 5,628,744 A | 5/1997 | Coleman et al. | | 5,949,222 A | 9/1999 | Buono |
| 5,630,811 A | 5/1997 | Miller | | 5,954,710 A | 9/1999 | Paolini et al. |
| 5,634,711 A | 6/1997 | Kennedy et al. | | 5,955,490 A | 9/1999 | Kennedy et al. |
| 5,649,972 A | 7/1997 | Hochstein | | 5,957,915 A | 9/1999 | Trost |
| 5,652,481 A | 7/1997 | Johnson et al. | | 5,964,749 A | 10/1999 | Eckhouse et al. |
| 5,653,706 A | 8/1997 | Zavislan et al. | | 5,968,033 A | 10/1999 | Fuller et al. |
| 5,655,547 A | 8/1997 | Karni | | 5,968,034 A | 10/1999 | Fullmer et al. |
| 5,657,760 A | 8/1997 | Ying et al. | | 5,974,616 A | 11/1999 | Dreyfus |
| 5,658,148 A | 8/1997 | Neuberger et al. | | 5,977,723 A | 11/1999 | Yoon |
| 5,658,323 A | 8/1997 | Miller | | 5,979,454 A | 11/1999 | Anvari et al. |
| 5,660,836 A | 8/1997 | Knowlton | | 5,984,915 A | 11/1999 | Loeb et al. |
| 5,661,744 A | 8/1997 | Murakami et al. | | 6,007,219 A | 12/1999 | O'Meara |
| 5,662,643 A | 9/1997 | Kung et al. | | 6,015,404 A | 1/2000 | Altshuler et al. |
| 5,662,644 A | 9/1997 | Swor | | 6,022,316 A | 2/2000 | Eppstein et al. |
| 5,673,451 A | 10/1997 | Moore et al. | | 6,026,828 A | 2/2000 | Altshuler |
| 5,679,113 A | 10/1997 | Caisey et al. | | 6,027,495 A | 2/2000 | Miller |
| 5,683,380 A | 11/1997 | Eckhouse et al. | | 6,029,303 A | 2/2000 | Dewan |
| 5,698,866 A | 12/1997 | Doiron et al. | | 6,029,304 A | 2/2000 | Hulke et al. |
| 5,707,401 A | 1/1998 | Martin et al. | | 6,030,378 A | 2/2000 | Stewart |
| 5,707,403 A | 1/1998 | Grove et al. | | 6,030,399 A | 2/2000 | Ignotz et al. |
| 5,713,738 A | 2/1998 | Yarborough | | 6,032,071 A | 2/2000 | Binder |
| 5,714,119 A | 2/1998 | Kawagoe et al. | | RE36,634 E | 3/2000 | Ghaffari |
| 5,720,772 A | 2/1998 | Eckhouse | | 6,036,684 A | 3/2000 | Tankovich et al. |
| 5,722,397 A | 3/1998 | Eppstein | | 6,044,514 A | 4/2000 | Kaneda et al. |
| 5,725,522 A | 3/1998 | Sinofsky | | 6,050,990 A | 4/2000 | Tankovich et al. |
| 5,728,090 A | 3/1998 | Martin et al. | | D424,197 S | 5/2000 | Sydlowski et al. |
| 5,735,844 A | 4/1998 | Anderson et al. | | 6,056,548 A | 5/2000 | Neuberger et al. |
| 5,735,884 A | 4/1998 | Thompson et al. | | 6,056,738 A | 5/2000 | Marchitto et al. |
| 5,738,678 A | 4/1998 | Patel | | 6,058,937 A | 5/2000 | Doiron et al. |
| 5,742,392 A | 4/1998 | Anderson et al. | | 6,059,820 A | 5/2000 | Baronov |
| 5,743,901 A | 4/1998 | Grove et al. | | 6,063,108 A | 5/2000 | Salansky et al. |
| 5,743,902 A | 4/1998 | Trost | | 6,070,092 A | 5/2000 | Kazama et al. |
| 5,746,735 A | 5/1998 | Furumoto et al. | | 6,074,382 A | 6/2000 | Asah et al. |
| 5,755,751 A | 5/1998 | Eckhouse | | 6,080,146 A | 6/2000 | Altshuler et al. |
| 5,759,200 A | 6/1998 | Azar | | 6,080,147 A | 6/2000 | Tobinick |
| 5,769,076 A | 6/1998 | Maekawa et al. | | 6,086,363 A | 7/2000 | Moran et al. |
| 5,782,249 A | 7/1998 | Weber et al. | | 6,086,580 A | 7/2000 | Mordon et al. |
| 5,802,136 A | 9/1998 | Carol | | 6,094,767 A | 8/2000 | Iimura |
| 5,810,801 A | 9/1998 | Anderson et al. | | 6,096,029 A | 8/2000 | O'Donnell, Jr. |
| 5,812,567 A | 9/1998 | Jeon et al. | | 6,096,209 A | 8/2000 | O'Brien et al. |
| 5,813,855 A | 9/1998 | Crisio, Jr. | | 6,099,521 A | 8/2000 | Shadduck |
| 5,814,008 A | 9/1998 | Chen et al. | | 6,104,959 A | 8/2000 | Spertell |
| 5,814,040 A | 9/1998 | Nelson et al. | | 6,106,293 A | 8/2000 | Wiesel |
| 5,814,041 A | 9/1998 | Anderson et al. | | 6,106,294 A | 8/2000 | Daniel |
| 5,817,089 A | 10/1998 | Tankovich et al. | | 6,110,195 A | 8/2000 | Xie et al. |
| 5,820,625 A | 10/1998 | Izawa et al. | | 6,113,559 A | 9/2000 | Klopotek |
| 5,820,626 A | 10/1998 | Baumgardner | | 6,117,129 A | 9/2000 | Mukai |
| 5,824,023 A * | 10/1998 | Anderson ........................ 607/88 | | 6,120,497 A | 9/2000 | Anderson et al. |
| 5,827,264 A | 10/1998 | Hohla | | 6,126,655 A | 10/2000 | Domankevitz et al. |
| 5,828,803 A | 10/1998 | Eckhouse | | 6,129,723 A | 10/2000 | Anderson et al. |
| 5,830,208 A | 11/1998 | Muller | | 6,135,774 A | 10/2000 | Hack et al. |
| 5,835,648 A | 11/1998 | Narciso, Jr. et al. | | 6,142,650 A | 11/2000 | Brown et al. |
| 5,836,877 A | 11/1998 | Zavislan | | 6,142,939 A | 11/2000 | Eppstein et al. |
| 5,836,999 A | 11/1998 | Eckhouse et al. | | 6,149,644 A | 11/2000 | Xie |
| 5,840,048 A | 11/1998 | Cheng | | 6,149,895 A | 11/2000 | Kutsch |
| 5,849,029 A | 12/1998 | Eckhouse et al. | | 6,159,236 A | 12/2000 | Biel |
| 5,851,181 A | 12/1998 | Talmor | | 6,162,055 A | 12/2000 | Montgomery et al. |
| 5,853,407 A | 12/1998 | Miller | | 6,162,211 A | 12/2000 | Tankovich et al. |
| 5,860,967 A | 1/1999 | Zavislan et al. | | 6,162,212 A | 12/2000 | Kreindel et al. |
| 5,868,731 A | 2/1999 | Budnik et al. | | 6,171,300 B1 | 1/2001 | Adams |
| 5,871,480 A | 2/1999 | Tankovich | | 6,171,301 B1 | 1/2001 | Nelson |

| | | |
|---|---|---|
| 6,171,302 B1 | 1/2001 | Talpalriu et al. |
| 6,171,332 B1 | 1/2001 | Whitehurst |
| 6,173,202 B1 | 1/2001 | Eppstein |
| 6,174,325 B1 | 1/2001 | Eckhouse |
| 6,176,854 B1 | 1/2001 | Cone |
| 6,183,434 B1 | 2/2001 | Eppstein |
| 6,183,500 B1 | 2/2001 | Kohler |
| 6,183,773 B1 | 2/2001 | Anderson |
| 6,187,001 B1 | 2/2001 | Azar et al. |
| 6,187,029 B1 | 2/2001 | Shapiro et al. |
| 6,197,020 B1 | 3/2001 | O'Donnell, Jr. |
| 6,200,134 B1 | 3/2001 | Kovac et al. |
| 6,200,309 B1 | 3/2001 | Rice et al. |
| 6,202,242 B1 | 3/2001 | Salmon et al. |
| 6,210,425 B1 | 4/2001 | Chen |
| 6,214,034 B1 | 4/2001 | Azar |
| 6,221,095 B1 | 4/2001 | Van Zuylen et al. |
| 6,228,075 B1 | 5/2001 | Furumoto |
| 6,229,831 B1 | 5/2001 | Nightingale et al. |
| 6,235,015 B1 | 5/2001 | Mead, III et al. |
| 6,235,016 B1 | 5/2001 | Stewart |
| 6,236,891 B1 | 5/2001 | Ingle et al. |
| 6,239,442 B1 | 5/2001 | Iimura et al. |
| 6,240,306 B1 | 5/2001 | Rohrscheib et al. |
| 6,245,093 B1 | 6/2001 | Li et al. |
| 6,251,127 B1 | 6/2001 | Biel |
| 6,263,233 B1 | 7/2001 | Zavislan et al. |
| 6,264,649 B1 | 7/2001 | Whitcroft et al. |
| 6,267,779 B1 | 7/2001 | Gerdes |
| 6,267,780 B1 | 7/2001 | Streeter |
| 6,273,884 B1 | 8/2001 | Altshuler et al. |
| 6,273,885 B1 | 8/2001 | Koop et al. |
| 6,280,438 B1 | 8/2001 | Eckhouse et al. |
| 6,283,956 B1 | 9/2001 | McDaniel |
| 6,290,496 B1 | 9/2001 | Azar et al. |
| 6,290,713 B1 | 9/2001 | Russell |
| 6,306,130 B1 | 10/2001 | Anderson et al. |
| 6,306,160 B1 | 10/2001 | Nidetzky |
| 6,315,772 B1 | 11/2001 | Marchitto et al. |
| 6,317,624 B1 | 11/2001 | Kollias et al. |
| 6,319,274 B1 | 11/2001 | Shadduck |
| 6,325,769 B1 | 12/2001 | Klopotek |
| 6,328,733 B1 | 12/2001 | Trost |
| 6,331,111 B1 | 12/2001 | Cao |
| 6,340,495 B1 | 1/2002 | Sumian et al. |
| 6,343,400 B1 | 2/2002 | Massholder et al. |
| 6,343,933 B1 | 2/2002 | Montgomery et al. |
| 6,350,261 B1 | 2/2002 | Domankevitz et al. |
| 6,350,276 B1 | 2/2002 | Knowlton |
| 6,354,370 B1 | 3/2002 | Miller et al. |
| 6,355,054 B1 | 3/2002 | Neuberger et al. |
| 6,358,242 B1 | 3/2002 | Cecchetti |
| 6,358,272 B1 | 3/2002 | Wilden |
| 6,383,176 B1 | 5/2002 | Connors et al. |
| 6,383,177 B1 | 5/2002 | Balle-Petersen et al. |
| 6,387,089 B1 | 5/2002 | Kreindel et al. |
| 6,387,353 B1 | 5/2002 | Jensen et al. |
| 6,395,016 B1 | 5/2002 | Oron et al. |
| 6,402,739 B1 | 6/2002 | Neev |
| 6,406,474 B1 | 6/2002 | Neuberger et al. |
| 6,413,267 B1 | 7/2002 | Dumoulin-White et al. |
| 6,416,319 B1 | 7/2002 | Cipolla |
| 6,419,389 B1 | 7/2002 | Fuchs et al. |
| 6,424,852 B1 | 7/2002 | Zavislan |
| 6,425,912 B1 | 7/2002 | Knowlton |
| 6,435,873 B1 | 8/2002 | Burgio |
| 6,436,094 B1 | 8/2002 | Reuter |
| 6,439,888 B1 | 8/2002 | Boutoussov et al. |
| 6,440,155 B1 | 8/2002 | Matsumae et al. |
| 6,443,978 B1 | 9/2002 | Zharov |
| 6,451,007 B1 | 9/2002 | Koop et al. |
| 6,461,296 B1 | 10/2002 | Desai |
| 6,471,712 B2 | 10/2002 | Burres |
| 6,471,716 B1 | 10/2002 | Pecukonis |
| 6,475,211 B2 | 11/2002 | Chess et al. |
| 6,484,052 B1 | 11/2002 | Visuri et al. |
| 6,485,413 B1 | 11/2002 | Boppart et al. |
| 6,494,900 B1 | 12/2002 | Salansky et al. |
| 6,497,702 B1 | 12/2002 | Bernaz |
| 6,503,486 B2 | 1/2003 | Xu et al. |
| 6,508,785 B1 | 1/2003 | Eppstein |
| 6,508,813 B1 | 1/2003 | Altshuler |
| 6,511,475 B1 | 1/2003 | Altshuler et al. |
| 6,514,243 B1 | 2/2003 | Eckhouse et al. |
| 6,517,532 B1 | 2/2003 | Altshuler et al. |
| 6,525,819 B1 | 2/2003 | Delawter et al. |
| 6,527,764 B1 | 3/2003 | Neuberger et al. |
| 6,530,915 B1 | 3/2003 | Eppstein et al. |
| 6,537,270 B1 | 3/2003 | Elbrecht et al. |
| 6,547,780 B1 | 4/2003 | Sinofsky |
| 6,551,346 B2 | 4/2003 | Crossley |
| 6,554,439 B1 | 4/2003 | Teicher et al. |
| 6,556,596 B1 | 4/2003 | Kim et al. |
| 6,558,372 B1 | 5/2003 | Altshuler |
| 6,561,808 B2 | 5/2003 | Neuberger et al. |
| 6,569,155 B1 | 5/2003 | Connors et al. |
| 6,570,893 B1 | 5/2003 | Libatique et al. |
| 6,572,634 B2 | 6/2003 | Koo |
| 6,572,637 B1 | 6/2003 | Yamazaki et al. |
| 6,595,934 B1 | 7/2003 | Hissong et al. |
| 6,600,951 B1 | 7/2003 | Anderson |
| 6,602,245 B1 | 8/2003 | Thiberg |
| 6,605,080 B1 | 8/2003 | Altshuler et al. |
| 6,605,083 B2 | 8/2003 | Clement et al. |
| 6,606,755 B1 | 8/2003 | Robinson et al. |
| 6,616,447 B1 | 9/2003 | Rizoiu et al. |
| 6,616,451 B1 | 9/2003 | Rizolu et al. |
| 6,618,531 B1 | 9/2003 | Goto et al. |
| 6,623,272 B2 | 9/2003 | Clemans |
| 6,623,513 B2 | 9/2003 | Biel |
| 6,629,971 B2 | 10/2003 | McDaniel |
| 6,629,989 B2 | 10/2003 | Akita |
| 6,632,219 B1 | 10/2003 | Baranov et al. |
| 6,635,075 B2 | 10/2003 | Li et al. |
| 6,641,578 B2 | 11/2003 | Mukai |
| 6,641,600 B1 | 11/2003 | Kohler |
| 6,648,904 B2 | 11/2003 | Altshuler et al. |
| 6,653,618 B2 | 11/2003 | Zenzie |
| 6,659,999 B1 | 12/2003 | Anderson et al. |
| 6,660,000 B2 | 12/2003 | Neuberger et al. |
| 6,663,620 B2 | 12/2003 | Altshuler et al. |
| 6,663,658 B1 | 12/2003 | Kollias et al. |
| 6,663,659 B2 | 12/2003 | McDaniel |
| 6,675,425 B1 | 1/2004 | Iimura et al. |
| 6,676,654 B1 | 1/2004 | Balle-Petersen et al. |
| 6,679,837 B2 | 1/2004 | Daikuzono |
| 6,685,639 B1 | 2/2004 | Wang et al. |
| 6,685,699 B1 | 2/2004 | Eppstein et al. |
| 6,689,124 B1 | 2/2004 | Thiberg |
| 6,699,040 B1 | 3/2004 | Hahn et al. |
| 6,706,035 B2 | 3/2004 | Cense et al. |
| 6,709,269 B1 | 3/2004 | Altshuler |
| 6,709,446 B2 | 3/2004 | Lundahl et al. |
| 6,723,090 B2 | 4/2004 | Altshuler et al. |
| 6,743,222 B2 | 6/2004 | Durkin et al. |
| 6,746,444 B2 | 6/2004 | Key |
| 6,749,623 B1 | 6/2004 | Hsi et al. |
| 6,770,069 B1 | 8/2004 | Hobart et al. |
| 6,790,205 B1 | 9/2004 | Yamazaki et al. |
| 6,801,595 B2 | 10/2004 | Grodzins et al. |
| 6,808,331 B2 | 10/2004 | Hall et al. |
| 6,808,532 B2 | 10/2004 | Andersen et al. |
| RE38,670 E | 12/2004 | Asah et al. |
| 6,858,009 B2 | 2/2005 | Kawata et al. |
| 6,860,879 B2 | 3/2005 | Irion et al. |
| 6,862,771 B1 | 3/2005 | Muller |
| 6,863,781 B2 | 3/2005 | Nocera et al. |
| 6,878,144 B2 | 4/2005 | Altshuler et al. |
| 6,881,212 B1 | 4/2005 | Clement et al. |
| 6,887,260 B1 | 5/2005 | McDaniel |
| 6,888,319 B2 | 5/2005 | Inochkin et al. |
| 6,893,259 B1 | 5/2005 | Reizenson |
| 6,902,397 B2 | 6/2005 | Farrell et al. |
| 6,902,563 B2 | 6/2005 | Wilkens et al. |
| 6,936,046 B2 | 8/2005 | Hissong et al. |
| 6,942,658 B1 | 9/2005 | Rizoiu et al. |
| 6,953,341 B2 | 10/2005 | Black |
| 6,974,451 B2 | 12/2005 | Altshuler et al. |

| | | |
|---|---|---|
| 6,976,985 B2 | 12/2005 | Altshuler et al. |
| 6,989,023 B2 | 1/2006 | Black |
| 6,991,644 B2 | 1/2006 | Spooner et al. |
| 6,997,923 B2 | 2/2006 | Anderson et al. |
| 7,001,413 B2 | 2/2006 | Butler |
| 7,006,223 B2 | 2/2006 | Mullani |
| 7,029,469 B2 | 4/2006 | Vasily |
| 7,033,349 B2 | 4/2006 | Key |
| 7,041,100 B2 | 5/2006 | Kreindel |
| 7,044,959 B2 | 5/2006 | Anderson et al. |
| 7,060,061 B2 | 6/2006 | Altshuler et al. |
| 7,066,733 B2 | 6/2006 | Logan et al. |
| 7,070,611 B2 | 7/2006 | Biel |
| 7,077,840 B2 | 7/2006 | Altshuler et al. |
| 7,081,128 B2 | 7/2006 | Hart et al. |
| 7,097,639 B1 | 8/2006 | Almeida |
| 7,097,656 B1 | 8/2006 | Akopov et al. |
| 7,144,247 B2 | 12/2006 | Black |
| 7,144,248 B2 | 12/2006 | Irwin |
| 7,145,105 B2 | 12/2006 | Gaulard |
| 7,145,108 B2 | 12/2006 | Kanel et al. |
| 7,160,289 B2 | 1/2007 | Cohen |
| 7,198,634 B2 | 4/2007 | Harth et al. |
| 7,204,832 B2 | 4/2007 | Altshuler et al. |
| 7,220,254 B2 | 5/2007 | Altshuler et al. |
| 7,223,270 B2 | 5/2007 | Altshuler et al. |
| 7,223,281 B2 | 5/2007 | Altshuler et al. |
| 7,255,691 B2 | 8/2007 | Tolkoff et al. |
| 7,274,155 B2 | 9/2007 | Inochkin et al. |
| 7,291,140 B2 | 11/2007 | MacFarland et al. |
| 7,291,141 B2 | 11/2007 | Jay |
| 7,309,335 B2 | 12/2007 | Altshuler et al. |
| 7,311,722 B2 | 12/2007 | Larsen |
| 7,322,972 B2 | 1/2008 | Viator et al. |
| 7,329,273 B2 | 2/2008 | Altshuler et al. |
| 7,329,274 B2 | 2/2008 | Altshuler et al. |
| 7,331,964 B2 | 2/2008 | Maricle et al. |
| 7,333,698 B2 | 2/2008 | Israel |
| 7,351,252 B2 | 4/2008 | Altshuler et al. |
| 7,422,598 B2 | 9/2008 | Altshuler et al. |
| 7,431,719 B2 | 10/2008 | Altshuler et al. |
| 7,540,869 B2 | 6/2009 | Altshuler et al. |
| 7,624,640 B2 | 12/2009 | Maris et al. |
| 7,647,092 B2 | 1/2010 | Motz et al. |
| 7,763,016 B2 | 7/2010 | Altshuler et al. |
| 7,935,107 B2 | 5/2011 | Altshuler et al. |
| 8,002,768 B1 | 8/2011 | Altshuler et al. |
| 2001/0007068 A1 | 7/2001 | Ota et al. |
| 2001/0008973 A1 | 7/2001 | Van Zuylen et al. |
| 2001/0023363 A1 | 9/2001 | Harth et al. |
| 2001/0024777 A1 | 9/2001 | Azar et al. |
| 2001/0041886 A1 | 11/2001 | Durkin et al. |
| 2001/0046652 A1 | 11/2001 | Ostler et al. |
| 2001/0048077 A1 | 12/2001 | Afanassieva |
| 2002/0004066 A1 | 1/2002 | Stanley et al. |
| 2002/0005475 A1 | 1/2002 | Zenzie |
| 2002/0013572 A1 | 1/2002 | Berlin |
| 2002/0016587 A1 | 2/2002 | Furumoto |
| 2002/0018754 A1 | 2/2002 | Sagel et al. |
| 2002/0019624 A1 | 2/2002 | Clement et al. |
| 2002/0026225 A1 | 2/2002 | Segal |
| 2002/0029071 A1 | 3/2002 | Whitehurst |
| 2002/0049483 A1 | 4/2002 | Knowlton |
| 2002/0058890 A1 | 5/2002 | Visuri et al. |
| 2002/0071287 A1 | 6/2002 | Haase |
| 2002/0071827 A1 | 6/2002 | Petersen et al. |
| 2002/0072676 A1 | 6/2002 | Afanassieva |
| 2002/0081555 A1 | 6/2002 | Wiesel |
| 2002/0091377 A1 | 7/2002 | Anderson et al. |
| 2002/0108193 A1 | 8/2002 | Gruber |
| 2002/0111610 A1 | 8/2002 | Nordquist |
| 2002/0120256 A1 | 8/2002 | Furuno et al. |
| 2002/0123745 A1 | 9/2002 | Svaasand et al. |
| 2002/0128635 A1 | 9/2002 | Altshuler et al. |
| 2002/0128695 A1 | 9/2002 | Harth et al. |
| 2002/0161357 A1 | 10/2002 | Anderson et al. |
| 2002/0161418 A1 | 10/2002 | Wilkens et al. |
| 2002/0173780 A1 | 11/2002 | Altshuler et al. |
| 2002/0182563 A1 | 12/2002 | Boutoussov et al. |
| 2002/0183808 A1 | 12/2002 | Biel |
| 2003/0004499 A1 | 1/2003 | McDaniel |
| 2003/0009158 A1 | 1/2003 | Perricone |
| 2003/0009205 A1 | 1/2003 | Biel |
| 2003/0018373 A1 | 1/2003 | Eckhardt et al. |
| 2003/0023235 A1 | 1/2003 | Cense et al. |
| 2003/0023283 A1 | 1/2003 | McDaniel |
| 2003/0023284 A1 | 1/2003 | Gartstein et al. |
| 2003/0028227 A1 | 2/2003 | Neuberger et al. |
| 2003/0032900 A1 | 2/2003 | Ella |
| 2003/0032950 A1 | 2/2003 | Altshuler et al. |
| 2003/0036680 A1 | 2/2003 | Black |
| 2003/0040739 A1 | 2/2003 | Koop |
| 2003/0055414 A1 | 3/2003 | Altshuler et al. |
| 2003/0057875 A1 | 3/2003 | Inochkin et al. |
| 2003/0059738 A1 | 3/2003 | Neuberger |
| 2003/0065314 A1 | 4/2003 | Altshuler et al. |
| 2003/0083649 A1 | 5/2003 | Margaron et al. |
| 2003/0084534 A1 | 5/2003 | Kaizuka |
| 2003/0097122 A1 | 5/2003 | Ganz et al. |
| 2003/0100936 A1 | 5/2003 | Altshuler et al. |
| 2003/0104340 A1 | 6/2003 | Clemans |
| 2003/0109787 A1 | 6/2003 | Black |
| 2003/0109860 A1 | 6/2003 | Black |
| 2003/0113684 A1 | 6/2003 | Scott |
| 2003/0129154 A1 | 7/2003 | McDaniel |
| 2003/0130709 A1 | 7/2003 | D.C. et al. |
| 2003/0152528 A1 | 8/2003 | Singh et al. |
| 2003/0163884 A1 | 9/2003 | Weihrauch |
| 2003/0167080 A1 | 9/2003 | Hart et al. |
| 2003/0169433 A1 | 9/2003 | Koele et al. |
| 2003/0181896 A1 | 9/2003 | Zvuloni et al. |
| 2003/0187486 A1 | 10/2003 | Savage et al. |
| 2003/0195494 A1 | 10/2003 | Altshuler et al. |
| 2003/0199859 A1 | 10/2003 | Altshuler et al. |
| 2003/0216795 A1 | 11/2003 | Harth et al. |
| 2003/0232303 A1 | 12/2003 | Black |
| 2004/0006332 A1 | 1/2004 | Black |
| 2004/0010298 A1 | 1/2004 | Altshuler et al. |
| 2004/0015156 A1 | 1/2004 | Vasily |
| 2004/0015158 A1 | 1/2004 | Chen et al. |
| 2004/0019990 A1 | 2/2004 | Farrell et al. |
| 2004/0024388 A1 | 2/2004 | Altshuler |
| 2004/0024430 A1 | 2/2004 | Bader et al. |
| 2004/0030326 A1 | 2/2004 | Altshuler et al. |
| 2004/0034319 A1 | 2/2004 | Anderson et al. |
| 2004/0034341 A1 | 2/2004 | Altshuler et al. |
| 2004/0073079 A1 | 4/2004 | Altshuler et al. |
| 2004/0082940 A1 | 4/2004 | Black et al. |
| 2004/0085026 A1 | 5/2004 | Inochkin et al. |
| 2004/0093042 A1 | 5/2004 | Altshuler et al. |
| 2004/0093043 A1 | 5/2004 | Edel et al. |
| 2004/0111132 A1 | 6/2004 | Shenderova et al. |
| 2004/0116984 A1 | 6/2004 | Spooner et al. |
| 2004/0133251 A1 | 7/2004 | Altshuler et al. |
| 2004/0143920 A1 | 7/2004 | Nanda |
| 2004/0147984 A1 | 7/2004 | Altshuler et al. |
| 2004/0156626 A1 | 8/2004 | Thoms |
| 2004/0161213 A1 | 8/2004 | Lee |
| 2004/0162549 A1 | 8/2004 | Altshuler |
| 2004/0162596 A1 | 8/2004 | Altshuler et al. |
| 2004/0176754 A1 | 9/2004 | Island et al. |
| 2004/0191729 A1 | 9/2004 | Altshuler et al. |
| 2004/0193234 A1 | 9/2004 | Butler |
| 2004/0193235 A1 | 9/2004 | Altshuler et al. |
| 2004/0193236 A1 | 9/2004 | Altshuler et al. |
| 2004/0199227 A1 | 10/2004 | Altshuler et al. |
| 2004/0204745 A1 | 10/2004 | Altshuler et al. |
| 2004/0210276 A1 | 10/2004 | Altshuler et al. |
| 2004/0214132 A1 | 10/2004 | Altshuler |
| 2004/0225339 A1 | 11/2004 | Yaroslavsky et al. |
| 2004/0230258 A1 | 11/2004 | Altshuler et al. |
| 2004/0230260 A1 | 11/2004 | MacFarland et al. |
| 2004/0234460 A1 | 11/2004 | Tarver et al. |
| 2005/0038418 A1 | 2/2005 | Altshuler et al. |
| 2005/0049467 A1 | 3/2005 | Stamatas et al. |
| 2005/0049582 A1 | 3/2005 | DeBenedictis et al. |
| 2005/0049658 A1 | 3/2005 | Connors et al. |
| 2005/0063931 A1 | 3/2005 | Paus et al. |

| | | | | | | |
|---|---|---|---|---|---|---|
| 2005/0065531 A1 | 3/2005 | Cohen | EP | 0593 A | 2/1979 | |
| 2005/0085875 A1 | 4/2005 | Van Zuylen | EP | 0142671 A1 | 5/1985 | |
| 2005/0107849 A1 | 5/2005 | Altshuler et al. | EP | 0172490 A1 | 2/1986 | |
| 2005/0168158 A1 | 8/2005 | Inochkin et al. | EP | 0320080 A1 | 6/1989 | |
| 2005/0171517 A1 | 8/2005 | Altshuler et al. | EP | 0324120 A1 | 7/1989 | |
| 2005/0171581 A1 | 8/2005 | Connors et al. | EP | 0563953 | 10/1993 | |
| 2005/0177026 A1 | 8/2005 | Hoeg et al. | EP | 0565331 A2 | 10/1993 | |
| 2005/0182389 A1 | 8/2005 | LaPorte et al. | EP | 0598984 | 6/1994 | |
| 2005/0197681 A1 | 9/2005 | Barolet et al. | EP | 0709941 | 5/1996 | |
| 2005/0215988 A1 | 9/2005 | Altshuler et al. | EP | 0724894 A2 | 8/1996 | |
| 2005/0220726 A1 | 10/2005 | Pauly et al. | EP | 0726083 A2 | 8/1996 | |
| 2006/0004306 A1 | 1/2006 | Altshuler et al. | EP | 0736308 A2 | 10/1996 | |
| 2006/0004347 A1 | 1/2006 | Altshuler et al. | EP | 0743029 A2 | 11/1996 | |
| 2006/0009750 A1 | 1/2006 | Altshuler et al. | EP | 0755698 A2 | 1/1997 | |
| 2006/0020309 A1 | 1/2006 | Altshuler et al. | EP | 0763371 A2 | 3/1997 | |
| 2006/0047281 A1 | 3/2006 | Kreindel | EP | 0765673 A2 | 4/1997 | |
| 2006/0058712 A1 | 3/2006 | Altshuler et al. | EP | 0765674 A2 | 4/1997 | |
| 2006/0089687 A1 | 4/2006 | Spooner et al. | EP | 0783904 A2 | 7/1997 | |
| 2006/0094988 A1 | 5/2006 | Tosaya et al. | EP | 0884066 A2 | 12/1998 | |
| 2006/0122668 A1 | 6/2006 | Anderson et al. | EP | 0885629 A2 | 12/1998 | |
| 2006/0149343 A1 | 7/2006 | Altshuler et al. | EP | 0920840 A2 | 6/1999 | |
| 2006/0161143 A1 | 7/2006 | Altshuler et al. | EP | 1038505 A2 | 9/2000 | |
| 2006/0194164 A1 | 8/2006 | Altshuler et al. | EP | 1075854 | 2/2001 | |
| 2006/0206103 A1 | 9/2006 | Altshuler et al. | EP | 1138349 A2 | 10/2001 | |
| 2006/0253176 A1 | 11/2006 | Caruso et al. | EP | 1147785 A2 | 10/2001 | |
| 2006/0271028 A1 | 11/2006 | Altshuler et al. | EP | 1219258 A1 | 7/2002 | |
| 2006/0287646 A1 | 12/2006 | Altshuler et al. | EP | 1226787 A2 | 7/2002 | |
| 2007/0027440 A1 | 2/2007 | Altshuler et al. | EP | 1250893 | 10/2002 | |
| 2007/0038206 A1 | 2/2007 | Altshuler et al. | EP | 1057454 | 11/2003 | |
| 2007/0049910 A1 | 3/2007 | Altshuler et al. | EP | 1457234 | 9/2004 | |
| 2007/0060819 A1 | 3/2007 | Altshuler et al. | EP | 1495735 A1 | 1/2005 | |
| 2007/0067006 A1 | 3/2007 | Altshuler et al. | EP | 1512373 A1 | 3/2005 | |
| 2007/0073308 A1 | 3/2007 | Anderson et al. | EP | 1535582 A1 | 6/2005 | |
| 2007/0078501 A1 | 4/2007 | Altshuler et al. | EP | 1627662 A1 | 2/2006 | |
| 2007/0159592 A1 | 7/2007 | Rylander et al. | EP | 1839705 A1 | 10/2007 | |
| 2007/0185552 A1 | 8/2007 | Masotti et al. | EP | 1854505 A2 | 11/2007 | |
| 2007/0194717 A1 | 8/2007 | Belikov et al. | FR | 2199453 A1 | 4/1974 | |
| 2007/0198004 A1 | 8/2007 | Altshuler et al. | FR | 2591902 A1 | 6/1987 | |
| 2007/0213696 A1 | 9/2007 | Altshuler et al. | GB | 1546625 A | 5/1979 | |
| 2007/0213698 A1 | 9/2007 | Altshuler et al. | GB | 2044908 A | 10/1980 | |
| 2007/0213792 A1 | 9/2007 | Yaroslavsky et al. | GB | 2059053 A | 4/1981 | |
| 2007/0219604 A1 | 9/2007 | Yaroslavsky et al. | GB | 2059054 A | 4/1981 | |
| 2007/0219605 A1 | 9/2007 | Yaroslavsky et al. | GB | 2123287 A | 2/1984 | |
| 2007/0239142 A1 | 10/2007 | Altshuler et al. | GB | 2239675 A | 7/1991 | |
| 2007/0239143 A1 | 10/2007 | Altshuler et al. | GB | 2270159 A | 3/1994 | |
| 2007/0255355 A1 | 11/2007 | Altshuler et al. | GB | 2356570 A | 5/2001 | |
| 2007/0288071 A1 | 12/2007 | Rogers | GB | 2360461 A | 9/2001 | |
| 2008/0009842 A1 | 1/2008 | Manstein et al. | GB | 2360946 A | 10/2001 | |
| 2008/0058783 A1 | 3/2008 | Altshuler et al. | GB | 2364376 A | 1/2002 | |
| 2008/0132886 A1 | 6/2008 | Cohen et al. | GB | 2368020 A | 4/2002 | |
| 2008/0139901 A1 | 6/2008 | Altshuler et al. | GB | 2390021 A | 12/2003 | |
| 2008/0140164 A1 | 6/2008 | Oberreiter et al. | GB | 2397528 A | 7/2004 | |
| 2008/0172047 A1 | 7/2008 | Altshuler et al. | JP | 61058673 A | 3/1986 | |
| 2008/0183162 A1 | 7/2008 | Altshuler et al. | JP | 64-027554 A | 1/1989 | |
| 2008/0183250 A1 | 7/2008 | Tanojo et al. | JP | 1099574 A | 4/1989 | |
| 2008/0195183 A1 | 8/2008 | Botchkareva et al. | JP | 2174804 | 7/1990 | |
| 2008/0214988 A1 | 9/2008 | Altshuler et al. | JP | 3066387 A | 3/1991 | |
| 2008/0294150 A1 | 11/2008 | Altshuler et al. | JP | 199013014 A | 9/1991 | |
| 2008/0306471 A1 | 12/2008 | Altshuler et al. | JP | 6022871 | 2/1994 | |
| 2009/0048557 A1 | 2/2009 | Yeshurun et al. | JP | 07100219 A | 4/1995 | |
| 2009/0069741 A1 | 3/2009 | Altshuler et al. | JP | 9084803 A | 3/1997 | |
| 2011/0267830 A1 | 11/2011 | Altshuler et al. | JP | 09103508 A | 4/1997 | |
| | | | JP | 10014661 | 1/1998 | |
| FOREIGN PATENT DOCUMENTS | | | JP | 10-503109 A | 3/1998 | |
| AU | 1851583 A | 3/1984 | JP | 10165410 A | 6/1998 | |
| CN | 2053926 | 3/1990 | JP | 11047146 A | 2/1999 | |
| CN | 1073607 | 6/1993 | JP | 11081877 A | 3/1999 | |
| CN | 1182572 A | 5/1998 | JP | 2000037400 A | 2/2000 | |
| CN | 1351483 A | 5/2002 | JP | 2000-153003 A | 6/2000 | |
| CN | 1535126 A | 10/2004 | JP | 2000300684 A | 10/2000 | |
| DE | 3304230 A1 | 8/1984 | JP | 2001-029124 A | 2/2001 | |
| DE | 3719561 A1 | 1/1988 | JP | 2001145520 A | 5/2001 | |
| DE | 3837248 A1 | 5/1990 | JP | 2002506362 T | 2/2002 | |
| DE | 9102407 | 7/1991 | JP | 2003192809 A | 7/2003 | |
| DE | 19803460 | 8/1999 | JP | 2005027702 A | 2/2005 | |
| DE | 19944401 A1 | 3/2001 | RU | 2082337 C1 | 6/1997 | |
| DE | 10140715 A1 | 3/2002 | RU | 2089126 C1 | 9/1997 | |
| DE | 10112289 A1 | 9/2002 | RU | 2089127 C1 | 9/1997 | |
| DE | 10120787 | 1/2003 | RU | 2096051 C1 | 11/1997 | |

| | | |
|---|---|---|
| RU | 2122848 C1 | 12/1998 |
| WO | 8602783 | 5/1986 |
| WO | 88/04592 | 6/1988 |
| WO | 9000420 | 1/1990 |
| WO | 9102562 A1 | 3/1991 |
| WO | 91/13652 | 9/1991 |
| WO | 9216338 | 10/1992 |
| WO | 9219165 | 11/1992 |
| WO | 9305920 | 4/1993 |
| WO | 9510243 | 4/1995 |
| WO | 9515725 | 6/1995 |
| WO | 9532441 | 11/1995 |
| WO | 96/22741 A1 | 8/1996 |
| WO | 96/24406 A1 | 8/1996 |
| WO | 9623447 A1 | 8/1996 |
| WO | 9625979 | 8/1996 |
| WO | 9628212 A1 | 9/1996 |
| WO | 9636396 | 11/1996 |
| WO | 9641579 | 12/1996 |
| WO | 97/13458 | 4/1997 |
| WO | 97/13552 | 4/1997 |
| WO | 9713458 | 4/1997 |
| WO | 9722384 A1 | 6/1997 |
| WO | 98/07379 A1 | 2/1998 |
| WO | 9804317 | 2/1998 |
| WO | 9805286 A1 | 2/1998 |
| WO | 9805380 A1 | 2/1998 |
| WO | 9806456 | 2/1998 |
| WO | 98/20937 A2 | 5/1998 |
| WO | 9824507 | 6/1998 |
| WO | 98/41158 A1 | 9/1998 |
| WO | 9851235 A1 | 11/1998 |
| WO | 9852481 | 11/1998 |
| WO | 9858595 | 12/1998 |
| WO | 9910046 | 3/1999 |
| WO | 9917666 | 4/1999 |
| WO | 9917667 | 4/1999 |
| WO | 9927997 | 6/1999 |
| WO | 9929243 | 6/1999 |
| WO | 9934867 A1 | 7/1999 |
| WO | 9938569 | 8/1999 |
| WO | 9943387 | 9/1999 |
| WO | 9944638 A1 | 9/1999 |
| WO | 9946005 | 9/1999 |
| WO | 9949937 | 10/1999 |
| WO | 9962472 | 12/1999 |
| WO | 9966988 A1 | 12/1999 |
| WO | 0002491 | 1/2000 |
| WO | 0003257 A1 | 1/2000 |
| WO | 0007514 A1 | 2/2000 |
| WO | 0030714 A1 | 6/2000 |
| WO | 0032272 A1 | 6/2000 |
| WO | 0040266 A2 | 7/2000 |
| WO | 0041278 A1 | 7/2000 |
| WO | 0043070 A1 | 7/2000 |
| WO | 0044294 A1 | 8/2000 |
| WO | 0054649 A2 | 9/2000 |
| WO | 0054685 A2 | 9/2000 |
| WO | 0062700 A1 | 10/2000 |
| WO | 0064537 | 11/2000 |
| WO | 0066226 A1 | 11/2000 |
| WO | 0071045 A1 | 11/2000 |
| WO | 0074583 A1 | 12/2000 |
| WO | 0074781 A1 | 12/2000 |
| WO | 0078242 A1 | 12/2000 |
| WO | 0103257 A1 | 1/2001 |
| WO | 0114012 A1 | 3/2001 |
| WO | 0126573 A1 | 4/2001 |
| WO | 0134048 A1 | 5/2001 |
| WO | 0142671 A1 | 6/2001 |
| WO | 0154606 A1 | 8/2001 |
| WO | 0154770 | 8/2001 |
| WO | 0178830 A2 | 10/2001 |
| WO | 0209813 A1 | 2/2002 |
| WO | 0226147 A1 | 4/2002 |
| WO | 02053050 A1 | 7/2002 |
| WO | 02069825 A2 | 9/2002 |
| WO | 02078559 A1 | 10/2002 |
| WO | 02094116 A1 | 11/2002 |
| WO | 03005883 A2 | 1/2003 |
| WO | 03049633 A1 | 6/2003 |
| WO | 04000150 A1 | 12/2003 |
| WO | 2004/011848 A2 | 2/2004 |
| WO | 2004033040 A1 | 4/2004 |
| WO | 2004037068 A2 | 5/2004 |
| WO | 2004037287 A2 | 5/2004 |
| WO | 2004073537 | 9/2004 |
| WO | 2004080279 A2 | 9/2004 |
| WO | 2004084752 | 10/2004 |
| WO | 2004086947 | 10/2004 |
| WO | 2005007003 | 1/2005 |
| WO | 2005009266 A1 | 2/2005 |
| WO | 2005030317 A2 | 4/2005 |
| WO | 2005/046793 A2 | 5/2005 |
| WO | 2005065288 A2 | 7/2005 |
| WO | 2005/092438 A1 | 10/2005 |
| WO | 2005096981 A2 | 10/2005 |
| WO | 2005099369 A2 | 10/2005 |
| WO | 2005112815 A1 | 12/2005 |
| WO | 2006006123 A1 | 1/2006 |
| WO | 2006036968 A2 | 4/2006 |
| WO | 2006066226 A1 | 6/2006 |
| WO | 2006089227 A2 | 8/2006 |
| WO | 2006101735 A1 | 9/2006 |
| WO | 2006116141 A1 | 11/2006 |
| WO | 2007/035444 A2 | 3/2007 |
| WO | 2007122611 A2 | 11/2007 |
| WO | 2008/070747 A2 | 6/2008 |

OTHER PUBLICATIONS

"BIOPTRON Light Therapy System," website print-out, accessed Jul. 13, 2006 (2 pages).

Altshuler et al., "Human Tooth as an Optical Device," SPIE vol. 1429 Holography and Interferometry and Optical Pattern Recognition in Biomedicine, pp. 95-104, 1991.

Altshuler et al., "Modern Optics and Dentistry," Laser in Dentistry, pp. 283-297, 1995.

Altshuler et al., "New Optical Effects in the Human Hard Tooth Tissues," Lasers and Medicine, Proc. SPIE vol. 1353, pp. 97-102, 1989.

Apfelberg et al. "Analysis of Complications of Argon Laser Treatment for Port Wine Hemangiomas with Reference to Striped Technique," Lasers in Surgery and Medicine, 2:357-371 (1983).

Apfelberg et al. "Dot or Pointillistic Method for Improvement in Results of Hypertrophic Scarring in the Argon Laser Treatment of Portwine Hemangiomas," Lasers in Surgery and Medicine, 6:552-558 (1987).

Blankenau et al., "In Vivo Caries-Like Lesion Prevention with Argon Laser: Pilot Study," Journal of Clinical Laser Medicine and Surgery, vol. 17, No. 6, pp. 241-243, 1999.

Chan, E.K., "Effects of Compression on Soft Tissue Optical Properties," IEEE Journal of Selected Topics in Quantum Electronics, vol. 2, No. 4, pp. 943-950 (Dec. 1996).

Dabrowska, "Intravital Treatment of the Pulp with Stimulation Laser Biostimulation," Abstract Rocz-Akad-Med-Bialymst. Bialymst. 1997; 42(1): 168-76.

Dixon et al. "Hypertrophic Scarring in Argon Laser Treatment of Port-Wine Stains," Plastic and Reconstructive Surgery, 73:771-777 (1984).

Fiskerstrand, E.J. et al., "Hair Removal with Long Pulsed Diode Lasers: A Comparison Between Two Systems with Different Pulse Structures," Lasers in Surgery and Medicine, vol. 32, pp. 399-404, 2003.

Forrest-Winchester et al., "The Effect of Infrared Laser Radiation on Dentinal Permeability in vitro," Department of Dentistry, University of Queensland Dental School, pp. 1-8, 1992.

Ginsbach et al. "New Aspects in the Management of Benign Cutaneous Tumors," Laser 79 Opto-Electronics, Munich Conference Proceedings, 344-347 (1979).

Gottlieb, I., "Power Supplies, Switching Regulators, Inverters & Converters," 1976.

Greenwald et al. "Comparative Histological Studies of the Tunable Dye (at 577 nm) Laser and Argon Laser: The Specific Vascular Effects of the Dye Laser," The Journal of Investigative Dermatology, 77:305-310 (1981).

Grossman, et al., "780 nm Low Power Diode Laser Irradiation Stimulates Proliferation of Keratinocyte Cultures: Involvement of Reactive Oxygen Species," Lasers in Surgery and Medicine vol. 29, pp. 212-218, 1998.

Grossman, M.C. et al., "Laser Targeted at Hair Follicles," Lasers Med Surg., Suppl. 7:221 (1995).

Hicks et al., "After Low Fluence Argon Laser and Flouride Treatment," Compendium, vol. 18, No. 6, Jun. 1997.

Hicks et al., "Enamel Carries Initiation and Progression Following Low Fluence (energy) and Argon Laser and Fluoride Treatment," The Journal of Clinical Pediatric Dentistry, vol. 20, No. 1 pp. 9-13, 1995.

Hsu et al., "Combined Effects of Laser Irradiation/Solution Flouride Ion on Enamel Demineralization," Journal of Clinical Laser Medicine and Surgery, vol. 16, No. 2 pp. 93-105, 1998.

Hulsbergen Henning et al. "Clinical and Histological Evaluation of Portwine Stain Treatment with a Microsecond-Pulsed Dye-Laser at 577 NM," Lasers in Surgery and Medicine, 4:375-380 (1984).

Hulsbergen Henning et al., "Port Wine Stain Coagulation Experiments with a 540-nm Continuous Wave Dye-Laser," Lasers in Surgery and Medicine, 2:205-210 (1983).

Ivanov, A.P. et al., "Radiation Propagation in Tissues and Liquids with Close Particle Packing," Zhurnal Prikladnoi Spektroskopii, vol. 47, No. 4, pp. 662-668 (Oct. 1987).

Kalivradzhiyan et al., "The Usage of Low Intensity Laser Radiation for the Treatment of the Inflammatory processes of the Oral Cavity Mucosa after Applying Removable Plate Dentures," SPIE vol. 1984 pp. 225-230.

Karu, "Cell Attachment to Extracellular Matrics is Modulated by Pulsed Radiation at 820 nm and Chemicals that Modify the Activity of Enzymes in the Plasma Membrane," Laser in Surgery and Medicine, vol. 29, pp. 274-281, 2001.

Karu, "Photobiological Fundamentals of Low-Power Laser Therapy," 8th Congress of International Society for Laser Surgery and Medicine, Mar. 30, 1987.

Kazmina et al., "Laser Prophlaxis and Treatment of Primary caries," SPIE vol. 1984, pp. 231-233.

Kozlov et al., "Laser in Diagnostics and Treatment of Microcirculation Disorders Under Parodontitis," SPIE vol. 1984, pp. 253-264.

Levin, G. et al., "Designing with hyseretic current-mode control," EDN Magazine, pp. 1-8, Apr. 11, 1996.

Levin, G. et al., "Designing with hyseretic current-mode control," EDN Magazine, pp. 1-8, Apr. 28, 1994.

Maegawa, et al., "Effects of Near-Infrared Low-Level Laser Irradiation on Microcirculation," Lasers in Surgery and Medicine, vol. 27, pp. 427-437, 2000.

Mamedova et al., "Microbiological Estimate of Parodontis Laser Therapy Efficiency," SPIE vol. 1984, pp. 247-249.

Manstein, D. et al., "Selective Photothermolysis of Lipid-Rich Tissue," American Society for Laser medicine and Surgery Abstracts, No. 17, American Society for Laser Medicine and Surgery Twenty-First Annual Meeting, Apr. 20-22, 2001, p. 6.

Marinelli et al., "Diode laser illuminated automotive lamp systems," SPIE Proceedings vol. 3285:170-177 (1998).

McDaniel, et al., "Hexascan: A New Robotized Scanning Laser Handpiece," Cutis, 45:300-305 (1990).

Nemeth, et al., "Copper vapor laser treatment of pigmented lesions," Lasers Surg. Med. Supp. 2:51 (1990).

Ohbayashi, "Stimulatory Effect of Laser Irradiation on Calcified Nodule Formation in Human Dental Pulp Fibroblasts," Abstract J-Endod. Jan. 1999; 25(1): 30-3.

Oleinik, et al., "Automatized Securing Definition for Laser Therapy Indications in Case of Non-complicated Caries," SPIE, vol. 1984, pp. 238-244.

Orchardson, "Effect of Pulsed Nd:YAG Laser Radiation on Action Potential Conduction in Nerve Fibres Inside Teeth in vitro," Abstract J-Dent. Jul.-Aug. 1998; 26(5-6): 421-6.

Osigo et al, "Phase Transitions of Rat Stratum Corneum Lipids by an Electron Paramagnetic Resonance Study and Relationship of Phase States to Drug Penetration," Biochimica et Biophysica Acta 1301:97-104 (1996).

Ozawa et al., "Stimulatory Effects of Low-Power Laser Irradiation on Bone Formation in vitro," SPIE vol. 1984, pp. 281-288.

Petrischev et al. "Clinical and Experimental Low-Intense Laser Therapy in Dentistry," SPIE, vol. 1984, pp. 212-214.

Petrischev et al., "Report on Low Intensity Laser Radiation Usage in Dentistry," SPIE vol. 1984, pp. 202-211.

Powell, "Laser Dental Decay Prevention: does it have a future?" SPIE vol. 3192, 1997.

Remillard et al., "Diode laser illuminated automotive brake lamp using a linear fanout diffractive optical element," Proc. of the Diffractive Optics and Micro-Optics Conference, OSA Technical Digest Series vol. 10, 192-194 (1998).

Remillard et al., "Diode Laser Illuminators for Night-Vision Applications," SPIE Proceedings vol. 4285:14-22 (2001).

Rohrer, "Evaluating the Safety and Efficacy of a Novel Light Based Hair Removal System," Lasers. Surg. Med. Supp.13:97 (2001).

Rotteleur, et al., "Robotized scanning laser handpiece for the treatment of port wine stains and other angiodysplasias," Lasers Surg. Med., 8:283-287 (1998).

Rubach et al., "Histological and Clinical Evaluation of Facial Resurfacing Using a Carbon Dioxide Laser With the Computer Pattern Generator," Arch Otolaryngol Head Neck Surg., 123:929-934 (1997).

Rylander, C.G. et al., "Mechanical Tissue Optical Clearing Devices: Enhancement of Light Penetration in Ex Vivo Porcine Skin and Adipose Tissue," Lasers in Surgery and Medicine, vol. 40, pp. 688-694 (2008).

Sandford et al., "Thermal Effects During Desensitisation of Teeth with Gallium-Aluminum-Arsenide Lasers," University of Queensland Dental School, Periodontology 15: 25-30 (1994).

Schindl, "Does Low Intensity Laser Irradiation Really Cause Cell Damage?" Laser in Surgery and Medicine vol. 22, pp. 105, 2001.

Sheehan-Dare, et al., "Lasers in Dermatology," British Journal of Dermatology, 129:1-8 (1993).

Shimizu et al., "Prospect of Relieving Pain Due to Tooth Movement During Orthodontic Treatment Utilizing a GA-AI As Diode Laser," SPIE vol. 1984, pp. 275-280.

Shumilovitch et al., "Influence of Low Intensity Laser Radiation Upon the Microflora of Carious Cavities and Root Canal," SPIE vol. 1984, pp. 215-220.

Sing, "Electroacupuncture and Laser Stimulation Treatment: Evaluation by Somatosensory Evoked Potential in Conscious Rabbits," Abstract AM-J-Chin-Med. 1997; 25(3-4): 263-71.

Sliney et al., "Safety with Lasers and Other Optical Sources: A Comprehensive Handbook," Plenum Press, pp. 477-480 (1980).

Sokolova et al., "Low-intense Laser Radiation in Complex Treatment of Inflammatory Diseases of Parodontium," SPIE vol. 1984, pp. 234-237.

Unger, "Laser Hair Transplantation III, Computer-assisted Laser Transplanting," Dermatol. Surg., 21:1047-1055 (1995).

Van Bruegel, "Power Density and Exposure Time of He-Ne Irradiation Are More Important Than Total Energy Dose in Photo-Biomodulation of Human Fibroblasts in Vitro," Lasers in Surgery and Medicine, vol. 12 pp. 528-537, 1992.

Walsh, "Laser "Curettage": a Critical Analysis," Periodontology 14:4-12, 1993.

Watanabe, S. et al., "The Effect of Pulse Duration on Selective Pigmented Cell Injury by Dye Lasers," The Journal of Investigative Dermatology, 88:523, 1987.

Westerman et al., "Argon Laser Irradiation Effects on Sound Root Surfaces: In Vitro Scanning Electron Microscopic Observations," Journal of Clinical Laser Medicine and Surgery, vol. 16, No. 2, pp. 111-115, 1998.

Zonios et al., "Skin Melanin, Hemoglobin, and Light Scattering Properties can be Quantitatively Assessed in Vivo Using Diffuse Reflectance Spectroscopy," Journal of Investigative Dermatology,117:1452-1457 (Dec. 2001).

European Search Report for European Patent Application Serial No. 10012972.5 dated Mar. 1, 2011.

European Search Report for European Patent Application Serial No. 10012971.7 dated Mar. 1, 2011.

Office Action for Chinese Patent Invention No. 200610093460 dated Jan. 15, 2010.

Office Action for Japanese Patent Application No. 2007-236503 dated Oct. 29, 2009.

GB. Altshuler et al., "Acoustic response of hard dental tissues to pulsed laser action," SPIE vol. 2080, Dental Application of Lasers, pp. 97-103, 1993.
G.B. Altshuler et al. "Extended theory of selective photothermolysis," Lasers in Surgery and Medicine, vol. 29, pp. 416-432, 2001.
R.L. Amy & R. Storb, "Selective mitochondrial damage by a ruby laser microbeam: An electron microscopic study," Science, vol. 15, pp. 756-758, Nov. 1965.
R. R. Anderson et al., "The optics of human skin," Journal of Investigative Dermatology, vol. 77, No. 1, pp. 13-19, 1981.
R.R. Anderson & J.A. Parish, "Selective photothermolysis: Precise microsurgery by selective absorption of pulsed radiation," Science, vol. 220, pp. 524-527, Apr. 1983.
A. V. Belikov et al., "Identification of enamel and dentine under tooth laser treatment," SPIE vol. 2623, Progress in Biomedical Optics Europt Series, Proceedings of Medical Applications of Lasers III, pp. 109-116, Sep. 1995.
J.S. Dover et al., "Pigmented guinea pig skin irradiated with Q-switched ruby laser pulses," Arch Dermatol, vol. 125, pp. 43-49, Jan. 1989.
L.H. Finkelstein & L.M. Blatstein, "Epilation of hair-bearing urethral grafts using the neodymium:yag surgical laser," Journal of Urology, vol. 146, pp. 840-842, Sep. 1991.
L. Goldman, Biomedical Aspects of the Laser, Springer-Verlag New York Inc., publishers, Chapts. 1, 2, & 23, 1967.
L. Goldman, "Dermatologic manifestations of laser radiation," Proceedings of the First Annual Conference on Biologic Effects of Laser Radiation, Federation of American Societies for Experimental Biology, Supp. No. 14, pp. S-92-S-93, Jan.-Feb. 1995.
L. Goldman, "Effects of new laser systems on the skin," Arch Dermatol., vol. 108, pp. 385-390, Sep. 1973.
L. Goldman, "Laser surgery for skin cancer," New York State Journal of Medicine, pp. 1897-1900, Oct. 1977.
L. Goldman, "Surgery by laser for malignant melanoma," J. Dermatol. Surg. Oncol., vol. 5, No. 2, pp. 141-144, Feb. 1979.
L. Goldman, "The skin", Arch Environ Health, vol. 18, pp. 434-436, Mar. 1969.
L. Goldman & D.F. Richfield, "The effect of repeated exposures to laser beams," Acta derm.-vernereol., vol. 44, pp. 264-268, 1964.
L. Goldman & R.J. Rockwell, "Laser action at the cellular level," JAMA, vol. 198, No. 6, pp. 641-644, Nov. 1966.
L. Goldman & R.G. Wilson, "Treatment of basal cell epithelioma by laser radiation," JAMA, vol. 189, No. 10, pp. 773-775.
L. Goldman et al., The biomedical aspects of lasers, JAMA, vol. 188, No. 3, pp. 302-306, Apr. 1964.
L. Goldman et al., "Effect of the laser beam on the skin, Preliminary report" Journal of Investigative Dermatology, vol. 40, pp. 121-122, 1963.
L. Goldman et al., "Effect of the laser beam on the skin, III. Exposure of cytological preparations," Journal of Investigative Dermatology, vol. 42, pp. 247-251, 1964.
L. Goldman et al., "Impact of the laser on nevi and melanomas," Archives of Dermatology, vol. 90, pp. 71-75, Jul. 1964.
L. Goldman et al., "Laser treatment of tattoos, A preliminary survey of three year's clinical experience," JAMA, vol. 201, No. 11, pp. 841-844, Sep. 1967.
L. Goldman et al., "Long-term laser exposure of a senile freckle," ArchEnviron Health, vol. 22, pp. 401-403, Mar. 1971.
L. Goldman et al., "Pathology, Pathology of the effect of the laser beam on the skin," Nature, vol. 197, No. 4870, pp. 912-914, Mar. 1963.
L. Goldman et al., "Preliminary investigative of fat embolization from pulsed ruby laser impacts of bone," Nature, vol. 221, pp. 361-363, Jan. 1969.
L. Goldman et al., "Radiation from a Q-switched ruby laser, Effect of repeated impacts of power output of 10 megawatts on a tattoo of man," Journal of Investigative Dermatology, vol. 44, pp. 69-71, 1965.
L. Goldman et al., "Replica microscopy and scanning electron microscopy of laser impacts on the skin," Journal of Investigative Dermatology, vol. 52, No. 1, pp. 18-24, 1969.

M. C. Grossman et al., "Damage to hair follicles by normal-mode ruby laser pulses," Journal of he American Academy of Dermatology, vol. 35, No. 6, pp. 889-894, Dec. 1996.
E. Klein et al., "Biological effects of laser radiation 1.," Northeast Electronics Research and Engineering Meeting, NEREM Record, IEEE catalogue No. F-60, pp. 108-109, 1965.
J.G. Kuhns et al., "Laser injury in skin," Laboratory Investigation, vol. 17, No. 1, pp. 1-13, Jul. 1967.
J.G. Kuhns et al., "Biological effects of laser radiation II Effects of laser irradiation on the skin," NEREM Record, pp. 152-153, 1965.
R.J. Margolis et al., "Visible action spectrum for melanin-specific selective photothermolysis," Lasers in Surgery and Medicine, vol. 9, pp. 389-397, 1989.
J.A. Parrish, "Selective thermal effects with pulsed irradiation from lasers: From organ to organelle," Journal of Investigative Dermatology, vol. 80, No. 6 Supplement, pp. 75s-80s, 1983.
L. Polla et al., "Melanosomes are a primary target of Q-switched ruby laser irradiation in guinea pig skin," Journal of Investigative Dermatology, vol. 89, No. 3, pp. 281-286, Sep. 1987.
T. Shimbashi & T. Kojima, "Ruby laser treatment of pigmented skin lesions," Aesth. Plast. Surg., vol. 19, pp. 225-229, 1995.
Stratton, K., et al., "Biological Effects of Laser Radiation II: ESR Studies of Melanin Containing Tissues after Laser Irradiation," Northeast Electronics Research and Engineering Meeting—NEREM Record, IEEE Catalogue No. F-60, pp. 150-151, Nov. 1965.
C.R. Taylor et al., "Treatment of tattoos by Q-switched ruby laser," Arch. Dermatol. vol. 126, pp. 893-899, Jul. 1990.
V.V. Tuchin, "Laser light scattering in biomedical diagnostics and therapy," Journal of Laser Applications, vol. 5, No. 2-3, pp. 43-60, 1993.
S. Watanabe et al, "Comparative studies of femtosecond to microsecond laser pulses on selective pigmented cell injury in skin," Photochemistry and Photobiology, vol. 53, No. 6, pp. 757-762, 1991.
A.J. Welch et al., "Evaluation of cooling techniques for the protection of the pidermis during HD-yag laser irradiation of the skin," Neodymium-Yag Laser in Medicine and Surgery, Elsevier Science Publishing Co., publisher, pp. 195-204, 1983.
R.B. Yules et al., "The effect of Q-switched ruby laser radiation on dermal tattoo pigment in man," Arch Surg, vol. 95, pp. 179-180, Aug. 1967.
G.G. Riggle et al., "Laser effects on normal and tumor tissue," Laser Applications in Medicine and Biology, vol. I, M.L. Wolbarsht, editor, Plenum Press, publishers, Chapter 3, pp. 35-65, 1971.
Abstracts Nos. 17-19, Lasers in Surgery and Medicine, ASLMS, Supplement 13, 2001.
P. Bjerring et al., "Selective Non-Ablative Wrinkle Reduction by Laser," J Cutan Laser Ther, vol. 2, pp. 9-15, 2000.
Doukas et al., "Transdermal Drug Delivery With a Pressure Wave," Advanced Drug Delivery Reviews 56 (2004), pp. 559-579.
Sumian, C.C. et al., "A Preliminary Clinical and Histopathological Study of Laser Skin Resurfacing Using a Frequency-Doubled Nd:YAG Laser After Application of Chromofilm.RTM.," Journal of Cutaneous Laser Therapy, vol. 1, pp. 159-166, 1999.
Sumian, C.C. et al., "Laser Skin Resurfacing Using a Frequency Doubled Nd:YAG Laser After Topical Application of an Exogenous Chromophore," Lasers in Surgery and Medicine, vol. 25, pp. 43-50, 1999.
E. Zeitler and M. L. Wolbarsht, "Laser Characteristics that Might be Useful in Biology," Laser Applications in Medicine and Biology, vol. I, M.L. Wolbarsht, editor, Plenum Press, publishers, Chapter 1, pp. 1-18, 1971.
US 6,230,044, 05/2001, Afanassieva et al. (withdrawn)

* cited by examiner

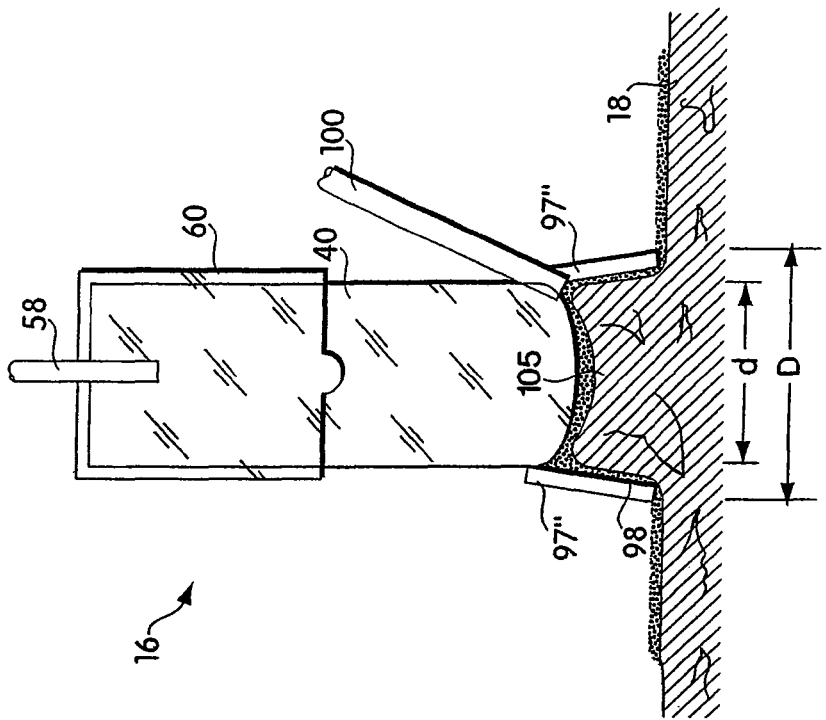
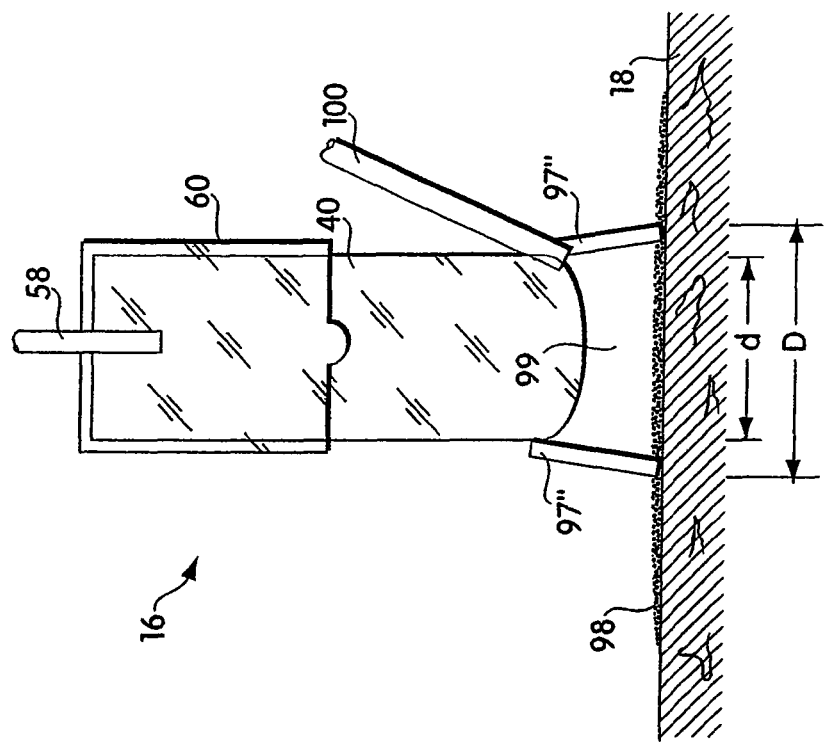

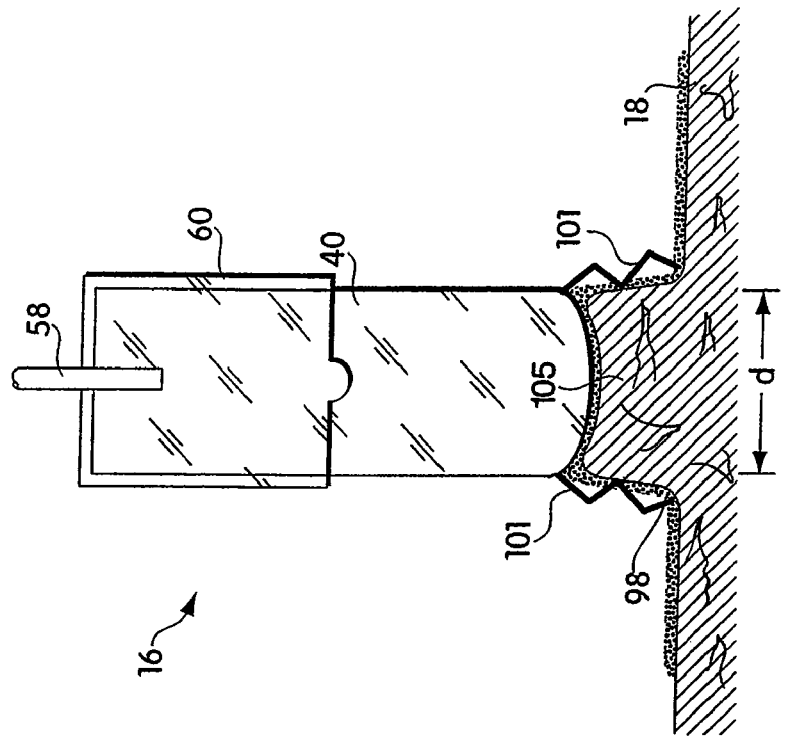
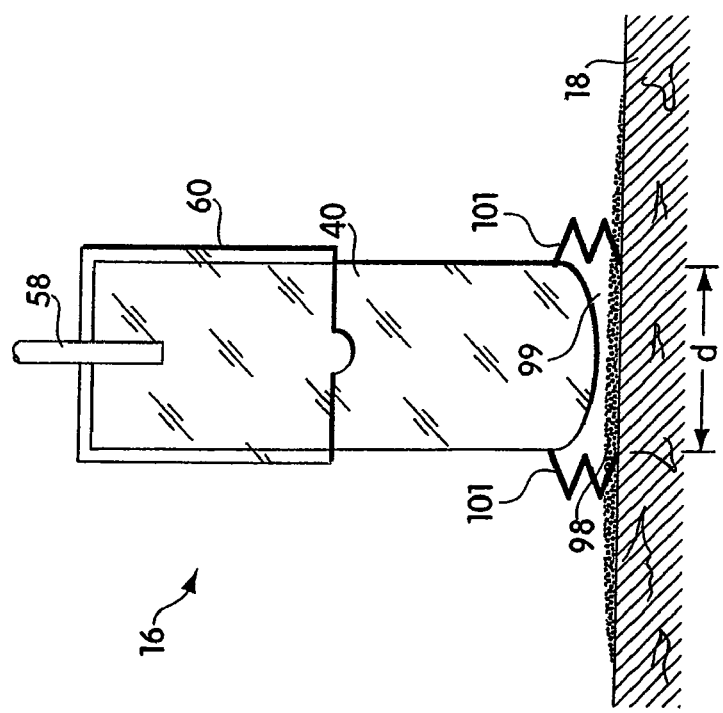

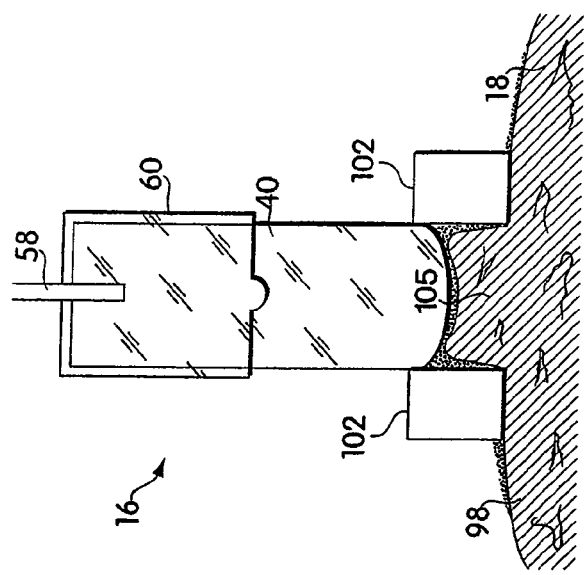
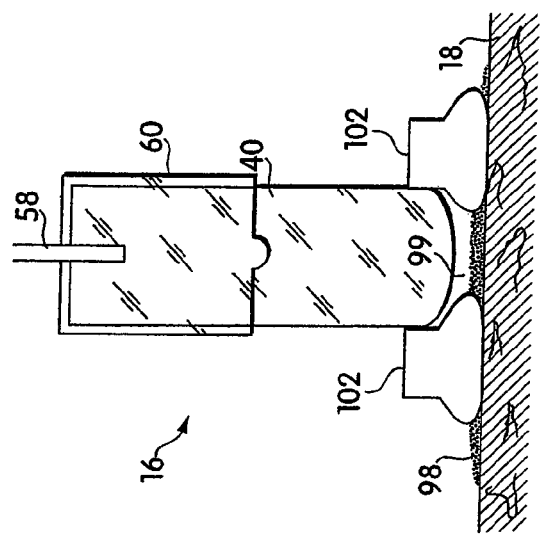
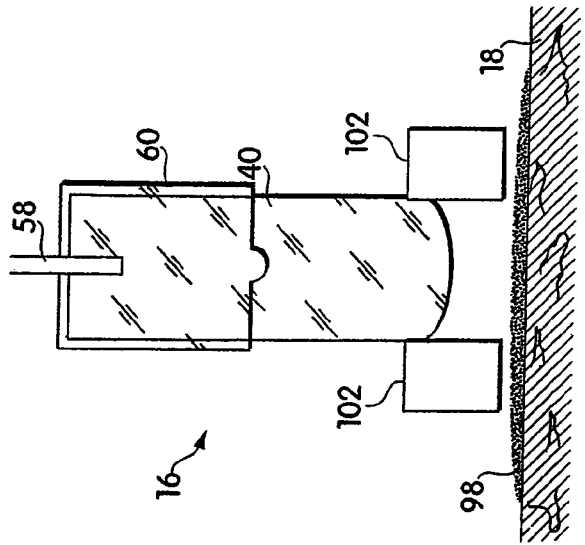

SYSTEM FOR ELECTROMAGNETIC RADIATION DERMATOLOGY AND HEAD FOR USE THEREWITH

RELATED APPLICATIONS

The present application is a continuation of patent application Ser. No. 11/093,693, filed Mar. 30, 2005 entitled "System for Electromagnetic Radiation Dermatology and Head for Use Therewith," which is a continuation of patent application Ser. No. 10/245,825 (U.S. Pat. No. 6,878,144), filed Sep. 17, 2002, which is in turn a continuation of patent application Ser. No. 09/268,433 (U.S. Pat. No. 6,508,813), filed Mar. 12, 1999, which application claims priority to Provisional Application 60/115,447, filed Jan. 8, 1999 and Provisional Application 60/077,794, filed Mar. 12, 1998. Said patent application Ser. No. 09/268,433 is also a continuation-in-part of patent application Ser. No. 08/759,036 (U.S. Pat. No. 6,015,404), filed Dec. 2, 1996; a continuation-in-part of patent application Ser. No. 08/759,136, filed Dec. 2, 1996, now abandoned; and a continuation-in-part of patent application Ser. No. 09/078,055 (U.S. Pat. No. 6,273,884), filed May 13, 1998, which application claims priority to Provisional Application 60/046,542, filed May 15, 1997; and Provisional Application 60/077,726, filed Mar. 12, 1998. The present application is also a continuation-in-part of patent application Ser. No. 09/473,910 (U.S. Pat. No. 6,517,532), filed Dec. 28, 1999, which application claims priority to Provisional Application 60/164,492, filed Nov. 9, 1999; and Provisional Application 60/115,447, filed Jan. 8, 1999. Said patent application Ser. No. 09/473,910 is also a continuation-in-part of said patent application Ser. No. 09/078,055 (U.S. Pat. No. 6,273,884), filed May 13, 1998, which application claims priority to Provisional Application 60/046,542, filed May 15, 1997; and Provisional Application 60/077,726, filed Mar. 12, 1998. The present application is also a continuation-in-part of patent application Ser. No. 09/634,981 (U.S. Pat. No. 6,511,475), filed Aug. 9, 2000, which application is a continuation of patent application Ser. No. 09/078,055 (U.S. Pat. No. 6,273,884), filed May 13, 1998, which application claims priority to Provisional Application 60/046,542, filed May 15, 1997; and Provisional Application 60/077,726, filed Mar. 12, 1998. The above applications to which the present application claims priority are herein incorporated by reference.

FIELD OF THE INVENTION

This invention relates to the utilization of electromagnetic (EM) radiation for treating selected dermatologic problems, and more particularly to a system which utilizes temperature detection at a waveguide through which radiation is being applied to the patient's skin to perform various control functions and to a head usable in such system or elsewhere, which head includes efficient reflectors for back-scattered radiation and/or for otherwise enhancing irradiation of a target volume containing the dermatologic problem.

BACKGROUND OF THE INVENTION

Lasers, lamps and other sources of electromagnetic radiation are being increasingly utilized to treat various dermatological conditions, and in particular for the removal of unwanted hair, spider veins, leg veins, other veins or blood vessels which are visible through the patient's skin, lesions, port-wine stains, tattoos and the like. One problem with such treatments is that the only way to get the radiation to a target volume in the dermis where treatment is desired is to transmit the radiation to such volume through the overlying epidermis. Further, since many of the treatments involve absorption of energy by melanin in the dermal volume being treated, for example in a hair follicle, and there is also melanin in the epidermis, particularly in the portion thereof at the dermal/epidermal (DE) junction, the EM radiation used for treatment is generally also absorbed to varying degrees in the epidermis. Further, the deeper in the dermis the treatment is desired and/or the larger the element being treated, the more energy must be used, this generally involving use of a more powerful laser or other radiation source with higher fluence and/or operating such source for longer time durations. However, as the energy applied through the epidermis increases, the potential for damage to the epidermis as a result of energy absorption therein also increases.

Therefore, one limitation on the energies which can be used for various dermatological treatments in the dermis, and in particular on the depths in the dermis at which treatment can be performed, and on the size of the elements which can be treated, is that the energy applied cannot be so high as to cause appreciable damage to the epidermis. Various ways around this problem have been proposed in the prior art, most of which involve some cooling of the epidermis prior to and/or during treatment to limit or prevent thermal damage thereto. Examples of such procedures include applying cryogenic or other cooling sprays to the skin, applying a cooling gel to the skin, applying radiation through a cold-pack in contact with the skin or through an applicator which is cooled by flowing water, flowing air, or the like. However, these prior art systems have not been wholly satisfactory. One reason for this is that, since most of the absorption is in the melanin located in the lower portions of the epidermis, it is desirable to have cooling through the entire epidermal layer, which is typically about 0.1 mm thick. However, it is not desirable that the cooling extend significantly below the DE junction into the dermal layer since cooling in the dermal layer can potentially inhibit the desired thermal damage to follicles, blood vessels or the like in this region. Further, there are significant variations in radiation absorption by a patients skin, not only among different individuals, people having darker skin absorbing more radiation and being more prone to epidermal damage than people with lighter skin, but even for different areas on the body of a single individual. Therefore, cooling which is not customized to the treatment area generally results in the cooling not being to the proper depth, a problem which can interfere with treatment and/or permit thermal damage to the epidermis.

It would therefore be desirable if the temperature at a selected depth in the skin, for example the DE junction, could be measured, and this temperature utilized to control skin temperature, for example through the epidermis, by some combination of controlling the laser energy applied to skin and/or controlling cooling applied to the skin. However, while infrared sensors have for example been utilized in the past to detect temperature at the surface of the skin, such detection does not provide an accurate indication of temperature even at the skin surface, these readings varying with such factors as skin layer thickness, skin roughness and skin color in addition to temperature. Infrared sensors also provide virtually no information as to skin temperature at a depth below the surface. Therefore, such detection has heretofore been used only for gross controls, for example to turn off the laser if an emergency temperature threshold is exceeded or the like, but not to fine tune energy application and/or cooling so as to maintain a desired temperature at a selected depth, for example at the DE junction, thereby facilitating a desired treatment without epidermal damage.

A need therefore exists for an improved technique which permits more accurate determinations of skin temperature at various depths, including at the DE junction, so as to permit more accurate and more automatic control of EM radiation treatments for various dermatological conditions. In particular, because of variations in skin pigmentation, differences in epidermal depth, and other dermatological differences among patients, laser dermatology procedures are now performed almost exclusively by physicians or other highly trained individuals, and such individuals must exercise great care to assure that epidermal damage does not occur, while still achieving the desired therapeutic effect. More accurate measurement of temperature at desired depths would make treatments by such skilled personnel easier to perform and would permit such procedures to be safely performed by less highly trained, and therefore less expensive, personnel. Such skin temperature measurements could also be utilized to determine skin type/pigmentation for the patient and/or for the part of a patient's body being treated and/or for other purposes.

Where cooling of the epidermis is achieved by placing a cooled applicator or other cooled body in contact with the patient's skin, the contact must be made with sufficient pressure to assure good thermal contact between the cooled body and the skin. However, differences in skin thickness and elasticity, differences in bone backing and other factors affect the pressure required to achieve good thermal contact for different patients and for different areas on the body for the same patient. This is another reason why highly trained and skilled individuals are required for performing the treatments and contributes to the high cost of the treatment. It would therefore be preferable if an automatic technique could be provided for detecting, and thus assuring, good thermal contact between a cooling element and the patient's skin. Such a technique or mechanism, by assuring good thermal contact with the skin before the radiation source is fired, could solve two critical safety problems for radiation dermatology. First, it assures adequate cooling of the epidermis before heating thereof through energy absorption; and second, it assures that the radiation will not be accidentally applied to the eyes or other unwanted place.

Related but opposite problems arise in performing certain skin resurfacing/wrinkle removal procedures where the objective is to heat and destroy only the most surface layer of the skin, for example the epidermis, with minimal damage to underlying layers. This requires tight control of factors such as laser energy, pulse duration and repetition rate. However, variations in patient's skin make such tight control difficult even for highly trained and skilled personnel. Similar problems also arise in other dermatological procedures involving lasers or other radiation sources.

Another related problem in using an EM radiation source for dermatological treatment is that the skin reflects back a significant portion of the radiation applied thereto. Since this reflected energy does not reach the treatment site, a higher energy radiation source is required to achieve the desired dermatological treatment than would be the case if a larger percentage of the applied radiation reached the treatment site. It has previously been suggested that one solution to this problem is to provide a retro-reflector which collects and returns such back-scattered radiation to the patient's skin. However, existing retro-reflector devices have not optimized the collection and return of such back-scattered radiation and improved techniques for the more efficient reutilization of back-scattered radiation is therefore desirable. One particular problem with prior art retroreflectors is that they reflect all back-scattered radiation at substantially the same angle the radiation was received; however, radiation at an angle more parallel than perpendicular to the skin surface generally does not reach the treatment area and therefore only heats the surface of the skin, contributing to thermal damage of the skin, without having any beneficial/therapeutic effect. A retroreflection technique which does not contribute to or increase this "parallel" radiation would therefore be desirable.

Two other factors can contribute to the efficiency of dermatologic treatments. The first factor is "spot size" or in other words the optical aperture of the applied radiation. Spot size is typically limited by the optics of the handpiece utilized and by the desired fluence as a function of the available energy source. However, a larger spot size permits treatment of large body areas such as back or legs to be accomplished much more quickly, something which enhances both patient satisfaction and practitioner profitability. A technique for facilitating larger spot sizes is thus desirable.

Secondly, anything which reduces the distance from the irradiation source to the target area reduces the amount of energy required to achieve a desired therapeutic effect and anything which permits more of the applied energy to reach the target area has a similar effect. Techniques which facilitate the achievements of these objectives are therefore also desirable.

SUMMARY OF THE INVENTION

In accordance with the above, this invention provides both a system for treating a selected dermatologic problem and a head for use in such system. The head, for preferred embodiments includes an optical waveguide or other light path for directing EM radiation of a wavelength appropriate for treating the selected patient dermatologic problem to a first end of the waveguide, the waveguide also having a skin-contacting second end which is opposite the first end; and a sensor at the second end of the waveguide, or otherwise closely adjacent a skin-contacting surface of the head, which senses the temperature thereat. For preferred embodiments, the head also includes a mechanism for removing heat from the waveguide. In order to achieve commercially useful sensitivity, it is preferable that the sensor be located no more than a few millimeters from the skin-contacting surface of the head, for example, the second end of the waveguide, the end contacting the patient's skin. Therefore, for preferred embodiments, the sensor is located within 5 mm of the second end of the waveguide, and for the most preferred embodiments the sensor is located within 1 mm of the second end.

Where a mechanism for removing heat is provided, such mechanism preferably includes a thermoelectric device having one side in thermal contact with the waveguide and an opposite side in thermal contact with a temperature sink. For a preferred embodiment of the invention, back-scattered radiation is substantially internally reflected within the optical waveguide, and there is a reflector within the waveguide for returning back-scattered radiation through the waveguide to the patient's skin. While the reflector may be at a variety of locations within the waveguide, for a preferred embodiment, it is located at the first end of the waveguide. The reflector may also be along sides of the waveguide and the coefficient of reflection for areas of the reflector, either at the first end, the side walls or both, may be selected such that back scattered radiation which, before entering the waveguide, at angles nearer perpendicular to the patient's skin are reflected more strongly than backscattered radiation which, before entering the waveguide, are at angles more nearly parallel to the skin surface. The second end of the waveguide in contact with the patient's skin may also have an aperture which is at least substantially as great as the aperture of radiation back-scattered from the patients skin or a "reflection aperture" substantially as great as the radiation back-scatter aperture may be achieved in other ways. For example, a reflector plate of size to provide the desired reflection aperture may surround the second end of the waveguide. More generally, the invention may include at least one waveguide passing through the head and terminating at a skin-contacting surface thereof, EM radiation being applied through the at least waveguide path to the patient's skin; and a reflection means for returning back-scattered radiation to the patients skin, which reflection means has a reflection aperture at least substantially as great as the radiation back-scatter aperture. Reflection means may include at least a portion of the skin-contacting surface of the head, which portion may be in the form of a reflection plate, and may also include at least one reflection surface for back-scattered radiation entering the waveguide, at least part of which surface may be in the waveguide.

The system may be for treating a selected dermatological problem in a selected volume of a patient's skin at a depth d which is below the DE junction. A source of EM radiation of a wavelength appropriate for treating the problem is provided along with an optical waveguide, a mechanism which cools the patient's skin, at least in the portion thereof in contact with the waveguide when the second end of the waveguide is in contact with the patient's skin, and a temperature sensor at the second end of the waveguide. The temperature at the sensor is indicative of the temperature at the patients DE junction. Finally, controls are provided which are operative in response to the sensor indicating that the DE junction has been cooled to at least a selected temperature for permitting radiation from the source to be passed through the waveguide to the patient's skin. The cooling mechanism preferably removes heat from the waveguide; when in contact with the patient's skin, the waveguide removing heat from and thus cooling the skin. The controls may also be operative in response to the sensor for maintaining the DE junction within a selected temperature range during application of radiation to the patient's skin. The controls may also detect a selected temperature/time profile at the sensor, the profile being indicative of contact of the waveguide with the patient's skin, and may prevent radiation from passing to the patient's skin unless the predetermined profile is detected. This assures that radiation is not applied to the patient's skin unless there is good thermal contact between the radiation-applying waveguide of the head and the patient's skin. For preferred embodiments, the controls operate the cooling mechanism to cool the waveguide to a desired temperature, the controls being responsive to the sensor for determining when the desired temperature has been reached.

The controls may also be operative in response to the sensor sensing a selected increasing temperature profile at the sensor when the waveguide is placed in contact with the patient's skin for permitting radiation from the source to be passed through the waveguide to the patient's skin. This control may be instead of the control based on detection that the DE junction has been cooled to a selected temperature, but is preferably in addition thereto.

The enhanced retro-reflector features discussed above may also be used in the head independent of the temperature measuring features previously discussed, but are preferably used in conjunction therewith. The invention may also include a head having at least one optical waveguide for receiving EM radiation and for directing it to a skin-contacting surface of the at least one waveguide and a standoff having a first and a second end, with the first end surrounding the at least one waveguide at its lower end and forming a substantially air-tight seal therewith. The second end of the standoff is adapted to be in contact with the patient's skin over the selected volume to form a chamber between the skin-contacting waveguide surface, the patients skin and walls of the standoff. A means is also provided for creating negative pressure in the chamber to draw the patient's skin therein and into contact with the skin-contact surface. The walls of the standoff are preferably reflective to return back-scattered radiation to the patient's skin. The means for creating negative pressure may include a hose mounted at one end to open into the chamber and connected at its other end to a source of negative pressure. Alternatively, the means for creating negative pressure may include the walls of the standoff being deformable when pressure is applied to the head/waveguide to permit the skin-contacting surface of the waveguide to contact the patient's skin, forcing most of the air from the chamber, with the walls of the standoff returning to their underformed state when pressure is released, resulting in the creation of negative pressure in the chamber. For example, the walls of the standoff may be in the form of a bellows, suction cup or elastic ring.

Finally, rather than a single optical waveguide, the output surface of a first optical waveguide to which irradiation is initially applied may be mounted to a first surface of a second optical waveguide which also has a second skin-contacting surface opposite the first surface. Optical radiation received from the first waveguide is transmitted through the second waveguide to the skin-contacting surface thereof. The second skin-contacting surface of the second waveguide has a larger area than the output surface of the first waveguide and the second waveguide is formed to provide a larger optical aperture than of the first waveguide. The ratio of the spacing between the first and second surfaces of the second waveguide and a selected surface dimension of the skin-contacting surface of the second waveguide, for example the length of a side of the second surface or a diameter thereof, is approximately 1.5 to 1. Means may be provided for reflecting radiation back-scattered from the patient's skin into the second waveguide back into the patient's skin. The means for reflecting may include forming at least a portion of the first surface and/or other surfaces of the second waveguide so as to reflect radiation impinging thereon, and such reflection from the second waveguide may also be made angle dependent.

The foregoing and other objects, features and advantages of the invention will be apparent from the following more particular description of preferred embodiments of the invention as illustrated in the accompanying drawings.

IN THE DRAWINGS

FIGS. 6a and 6b are simplified side sectional views of a head or applicator which utilizes negative pressure to draw a fold of skin into a cavity before negative pressure is applied and after negative pressure is applied respectively.

FIGS. 7a and 7b are simplified side sectional views of a head or applicator for another embodiment of the invention which utilizes negative pressure to draw a fold of skin into a cavity at an intermediate step in the creation of the negative pressure and after negative pressure has been created respectively.

FIGS. 8a, 8b and 8c are simplified side sectional views of a head or applicator for still another embodiment which uses negative pressure to draw a fold of skin into a chamber shown before negative pressure is created, at an intermediate stage in the creation of negative pressure and after negative pressure has been created respectively.

DETAILED DESCRIPTION

Figure 1:
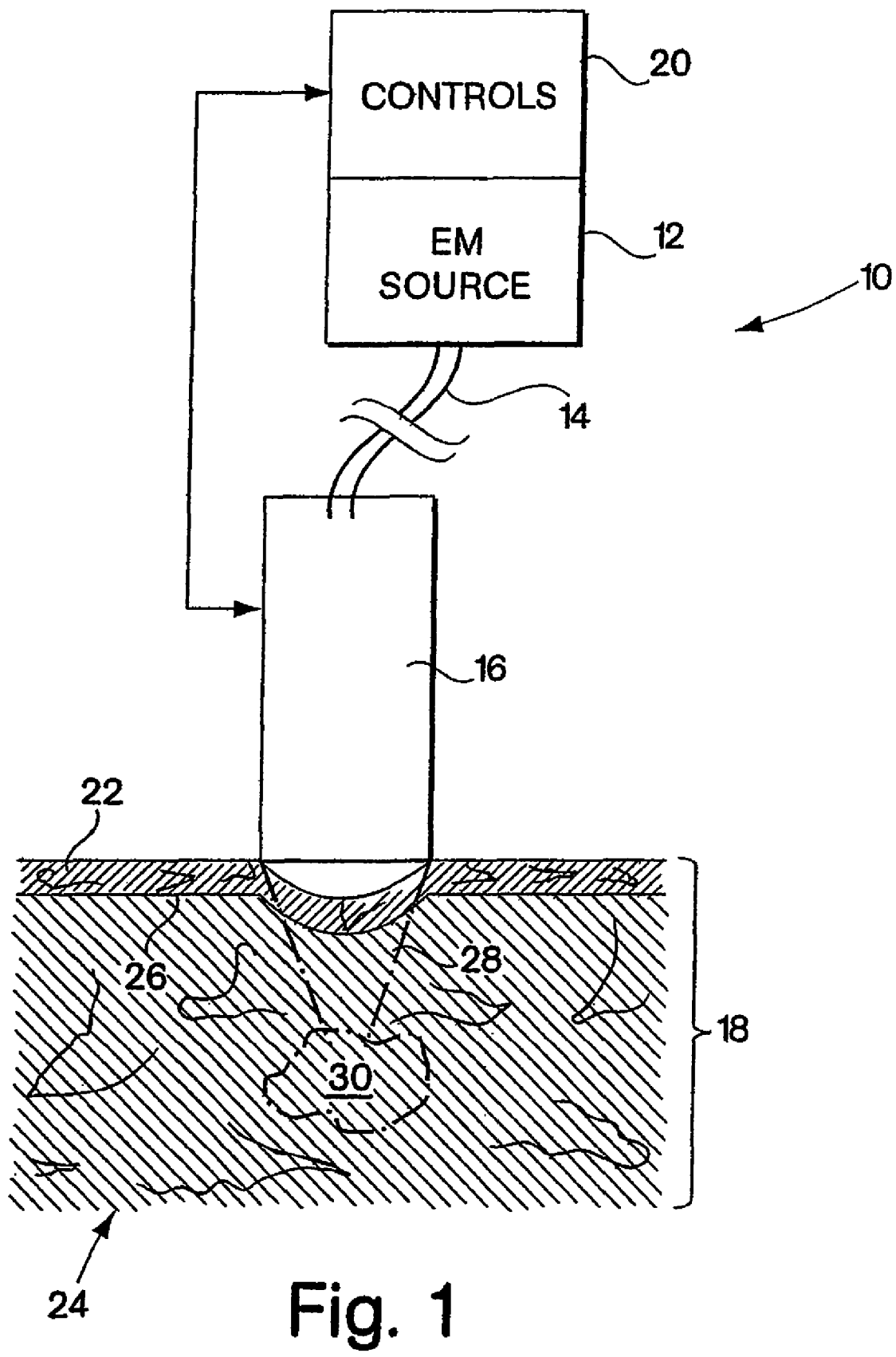
FIG. 1 is a schematic semi-block diagram of a simplified EM radiation treatment system suitable for use in practicing the teachings of this invention.

FIG. 1 is a simplified block diagram of a system 10 which may be utilized for treating a selected dermatological condition in accordance with the teachings of this invention. The system includes an electromagnetic (EM) radiation source 12 which is connected through a fiber optic light pipe or other suitable optical conveyor 14 to an applicator or head 16, which head is in contact with the skin 18 of a patient. Controls 20 are provided which receive information from source 12 and head 16 and which control operation of the system in response to these inputs and others. EM source 12 may be a ruby laser, alexandrite laser, diode laser or other laser source providing radiation of a suitable wavelength for the laser treatment to be performed, or may be a lamp or other non-coherent electromagnetic radiation source providing signals at the requisite wavelength. Particularly for non-coherent light sources, various techniques may be utilized to filter, frequency shift or otherwise control the output from the source to achieve radiation within a desired wavelength band. The radiation wavelength may be narrow band, down to a single wavelength, or wide band, and may vary over a wide spectrum from infrared through ultraviolet, depending on the treatment to be performed and the radiation source utilized. Source 12 may be a pulsed source, either under operator control or at a fixed or controlled repetition rate, or may, as taught in copending application Ser. No. 09/078,055, be a continuous wave (CW) source. Controls 20 may be a suitably programmed general purpose or special purpose computer, may be hard wired circuitry, or may be a hybrid of special purpose circuitry and programmed computer circuitry. Skin 18 has an epidermal layer 22, and a dermal layer 24, the junction of these two layers being sometimes referred to as the DE junction or basal layer 26.

Radiation from source 12 passes through head 16 and is emitted therefrom as a converging beam 28 which is applied to an area 30 in dermis 24 containing the element to be treated. Area 30 may, for example, contain a hair follicle which is to be destroyed in order to achieve removal of unwanted hair, may be tattoo pigment which is to be removed, may be a spider vein or other blood vessel which is to be coagulated and removed or may be some other dermatological condition which is to be treated by the radiation. As discussed earlier, treatment of a patient is complicated by the fact that there may be significant variations among patients, and in different areas of the body of the same patient, in the thickness of epidermal layer 22, in the pigmentation of this layer (and in particular in the quantity of melanin at DE junction 26), and in other characteristics of the skin. These variations make it difficult to achieve a desired therapeutic effect without potential damage to the area of the patient's epidermis overlying treatment area 30.

Figure 2:
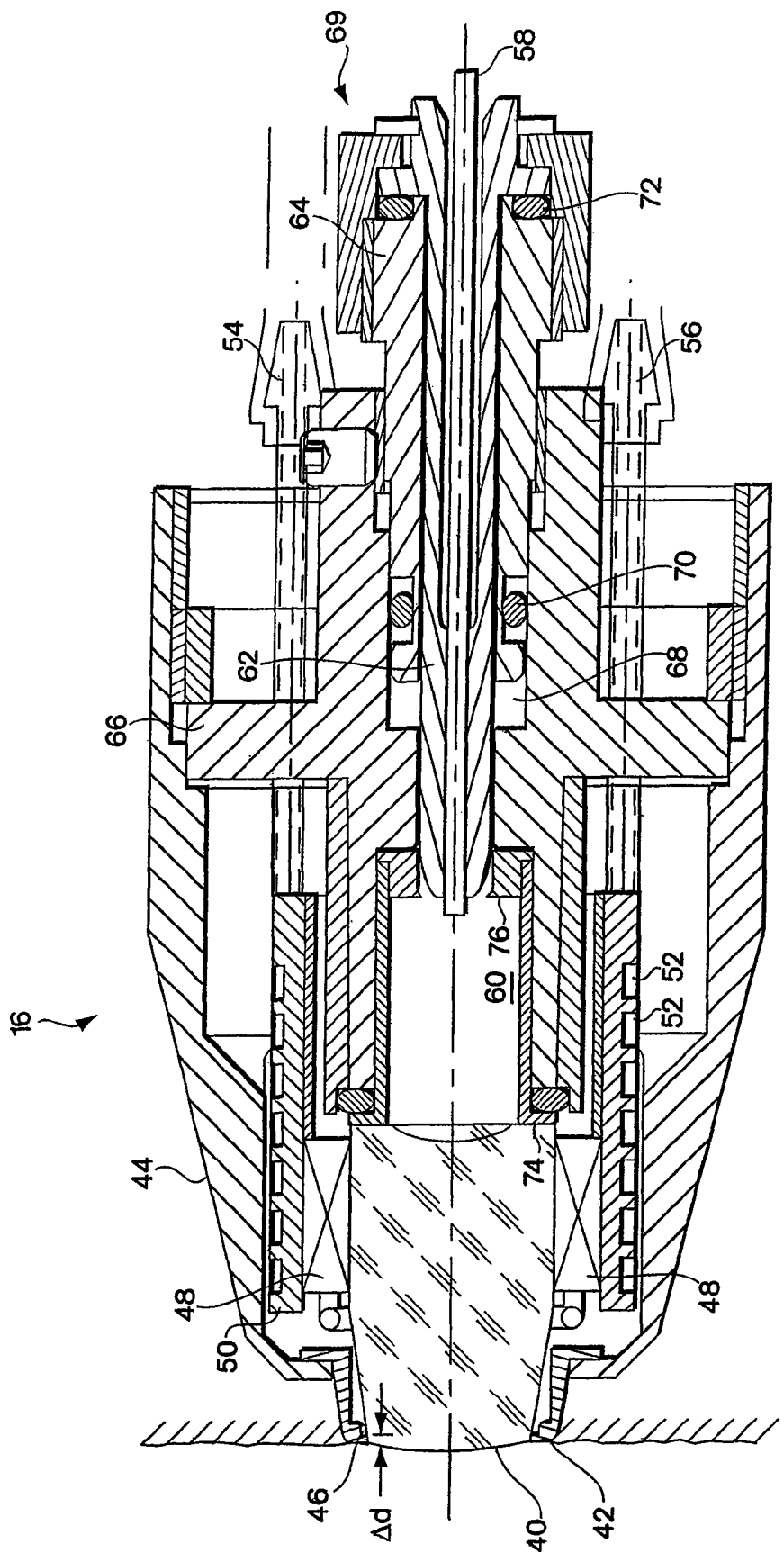
FIG. 2 is a side sectional view of a head or applicator suitable for use in the system of FIG. 1 in accordance with teachings of this invention.

FIG. 2 illustrates a head 16 suitable for use in the system of FIG. 1. Referring to FIG. 2, head 16 includes a waveguide or lens 40 of an optically transparent material which also has good heat transfer properties and preferably provides a good index of refraction match with skin. Sapphire is a currently preferred material for the waveguide, although other materials could also be used. Waveguide 40 is supported by a holder ring 42 mounted in an exterior housing 44. A thermocouple, thermistor or other suitable temperature sensor 46 is mounted in contact with waveguide 40, between the waveguide and holder 42. The distance ($\Delta d$) of sensor 46 from the end of waveguide 40 in contact with the patient's skin is critical and, for reasons to be discussed later, should be no more than 5 mm. $\Delta d$ is preferably in the 1-2 mm range, with approximately 1 mm being the currently preferred distance. While a single temperature sensor 46 is shown in FIG. 2, two or more such sensors spaced around waveguide 40 at the same distance $\Delta d$ from the end of the waveguide may be preferable to average out temperature variations which may occur in the waveguide.

Thermoelectric cooling elements 48 are also provided in contact with waveguide 40. While two such elements are shown in FIG. 2, typically at least four such elements, substantially evenly spaced around the periphery of waveguide 40, would normally be provided. Thermoelectric elements 48 may for example be Peltier elements. Electrical connections are made to sensor(s) 46 and to thermoelectric elements 48 in a manner known in the art and to simplify the figure are not specifically shown therein.

The sides of thermoelectric elements 48 opposite those in contact with waveguide 40 are in thermal contact with heat sink or radiator 50 having channels 52 formed therein through which a cooling fluid such as air or water flows, the cooling fluid entering the head through a fluid junction 54 and exiting through a fluid junction 56 (or entering though fluid junction 56 and exiting through fluid junction 54).

Optical radiation is applied to the head through an optical fiber, fiber bundle or other light pipe 58 which terminates at a chamber 60. Radiation exiting optical fiber 58 expands in chamber 60 before entering waveguide 40 for application to the patient's skin. Fiber 58 is mounted in a sleeve 62 of optically opaque material, the rear portion of which is mounted in a tube 64 and the forward portion of which extends through a holder assembly 66. Tube 64 is mounted in a chamber 68 formed in the rear of holder assembly 66 to permit assembly 69, which includes fiber 58, sleeve 62 and tube 64, to be moved forward and backward, moving fiber 58 in chamber 60 to adjust the optical aperture of the head. O-rings 70 and 72 seal chamber 60 to keep air and moisture out so as to avoid condensation on cooled optical surfaces 74 and 76. Nitrogen or another gas which does not condense at temperatures down to −40° C. is utilized to fill chamber 60.

Surface 74 of the waveguide is an optical reflecting surface as are all surfaces of chamber 60, including surface 76 at the rear thereof. As will be discussed later, these surfaces retroreflect back-scattered light from the patient's skin. The side walls of both waveguide 40 and chamber 60 may also be fully reflective or may selectively reflect in a manner and for reasons to be discussed later.

In operation, assembly 69 is initially positioned to achieve a desired optical aperture for head 16. Thermoelectric elements 48 are also energized to cool waveguide 40 to a selected temperature, for example 10° C. to −40° C. The criteria is to bring the waveguide 40 to a sufficiently low temperature to achieve the desired cooling of epidermis 22 without resulting in tissue temperature being brought down to a level where water in the cells might freeze. Good results have been achieved with a waveguide temperature in the 0° C. to −30° C. range, with a preferred temperature of approximately −10° C.

When the above preliminary steps have been completed, head 16 may be brought into physical contact with an area of the patient's skin where treatment is to be performed. This contact may be under low pressure, preferably at least sufficient to establish good thermal contact between waveguide 40 and the patient's skin, where the objective is to coagulate blood in for example a spider vein, leg vein or other vein or blood vessel, or may be under pressure greater than the patient's blood pressure for hair removal or other applications where it is preferable to remove blood from the region of skin between waveguide 40 and area 30 under treatment.

Figure 3A:
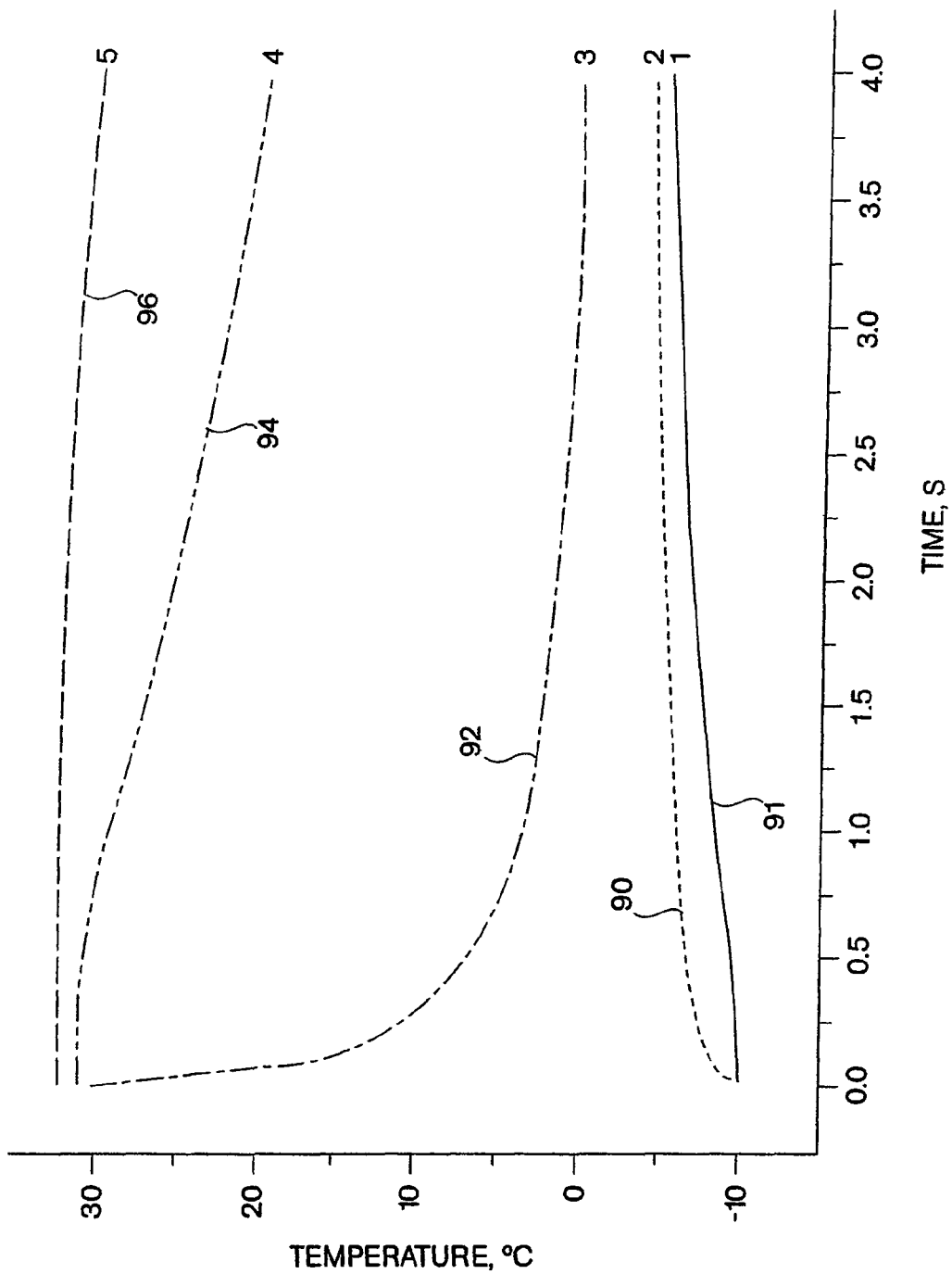
FIG. 3a is a graph illustrating a calculated relationship over time between the temperature at the waveguide at two Δd's where a sensor may be located and the temperature at three different depths in a patient's skin, including at the DE or basal junction.
Figure 3B:
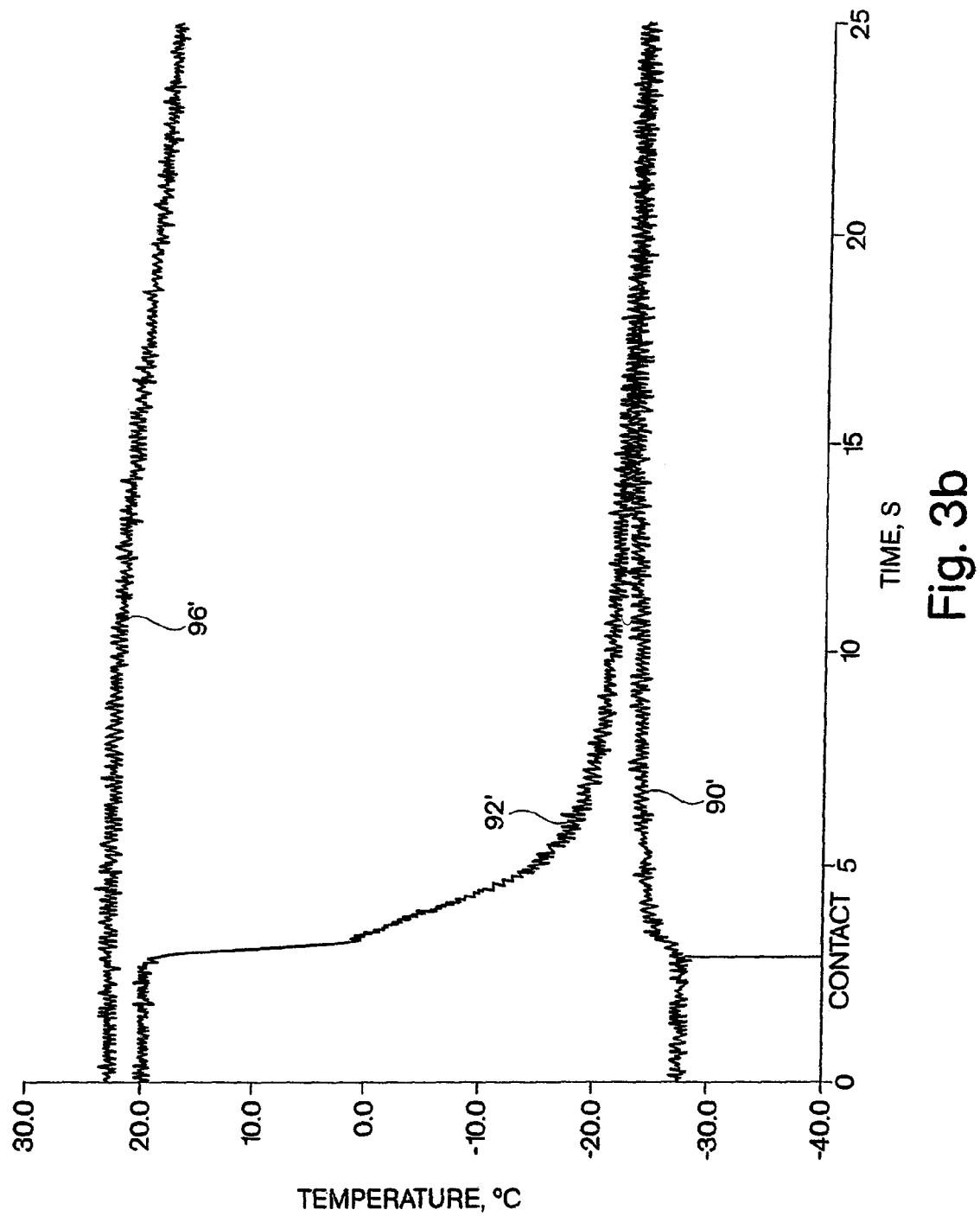
FIG. 3b is a graph illustrating a measured relationship over time between the temperature at the waveguide sensor for a preferred Δd and the temperature at two different depths in a patient's skin, including at the DE or basal junction.

In any event, head 16, and in particular waveguide 40 thereof, should be placed in contact with the patient's skin with sufficient pressure to assure good thermal contact between the patient's skin and waveguide 40. In accordance with the teachings of this invention, the fact that such good thermal contact has been established can be detected through use of sensor 46. In particular, as seen in FIGS. 3a and 3b, with the sensor positioned approximately 1 mm from the contact surface of waveguide 40, (i.e. $\Delta d = 1$ mm), the temperature at the sensor has a profile 90 in FIGS. 3a and 90' in FIG. 3b which increases sharply for the first quarter to one-half second after such thermal contact has been established. The reason for this is that the waveguide is acting as a heat sink for the patient's skin during this time interval and the heating of the waveguide at the skin-contacting end thereof is greater than the cooling effect of thermoelectric device 48 at this surface (i.e. there is a small temperature gradient across waveguide 40). The detection of the temperature profile 90, 90' by sensor(s) 46 can be interpreted by controls 20 as an indication of good thermal contact between the waveguide and the patient's skin. If such a thermal profile is not detected, controls 20 inhibit the activation of radiation source 12 and/or prevent radiation from the source being applied to head 16. This assures that radiation is not delivered to the skin unless the epidermis has been adequately cooled to prevent thermal damage thereto.

Referring for example to FIG. 3a, it is seen that the placement of sensor 46 relative to the skin-contacting surface of waveguide 40, or in other words the distance $\Delta d$, is critical in order to achieve this objective. In particular, while profile 90 is achieved for a $\Delta d$ of approximately 1.2 mm, profile 91, which is achieved with a $\Delta d$ of approximately 4.8 mm, evidences far less sensitivity to temperature changes at the DE junction and is therefore not particularly useful in assuring good thermal contact between the waveguide and the patient's skin. Actual profile 90' (FIG. 3b), while slightly more stepped and less smooth than the theoretical profile 90 of FIG. 3a, is sufficiently similar to this profile so as to permit easy identification of good thermal contact. Differences between FIGS. 3a and 3b may also arise from the fact that the waveguide in FIG. 3a starts at a temperature of −10° C. while the waveguide in FIG. 3b starts at a temperature of approximately −27° C.

Referring again to the Figures, and in particular to FIG. 3a, it is seen that a major portion of the waveguide cooling occurs within a period of between 0.5 and 2 seconds from full contact, the time varying somewhat with the initial temperature of the waveguide and the desired final temperature at the DE junction. Therefore, assuming good thermal contact has been made, an operator may operate source 12 some predetermined time after making contact with the patient's skin, for example a half second thereafter, but not more than approximately 2 seconds thereafter, to avoid significant cooling of the dermis.

However, since cooling of the skin may vary depending on a number of factors, including variations in the equipment being utilized, the color and nature of the patient's skin, the thickness of the patient's skin and the like, it is preferable that the temperature at the DE junction be measured and that the radiation source 12 be operated as soon as this temperature has dropped to a desired level. As can be seen from FIGS. 3a and 3b, the temperature profile 90 at sensor 46 tracks the temperature profile 92 at the DE junction as does the temperature profile 90' for DE junction temperature profile 92'. Thus, the output from sensor 46 can be utilized by control 20 as an indication of temperature at the DE junction, and radiation source 12 can be operated by control 20 when this temperature reaches a predetermined value. This assures that radiation is not applied to the patient until the patient's epidermis has been fully cooled to the desired level and that the operation of laser source 12 is not delayed so long as to cause cooling of portions of the follicle which are to be destroyed. In particular, 94 is a profile taken approximately 1 mm from the surface of the patient's skin, which is approximately the depth of the bulge in a hair follicle, and may be a depth where other dermatological treatments such as tattoo removal, treatment of port wine stain or vascular legions may occur. From FIG. 3a it is seen that for a time over two seconds, there is a significant drop in temperature at this depth, which can be 10° C. or more. For many dermatological applications, such a drop in temperature 1 mm into the dermis is undesirable, and in particular can adversely affect the desired treatment. Curves 96, 96' are temperature profiles with time deeper into the dermis, for example 2 mm therein. At this depth, the cooling effect of cooled waveguide 40 is not significant, perhaps a few degrees Celsius. This lack of cooling effect at deeper depths stems both from the greater distance of these point from the cooling source and from the proximity of tissue at this depth to the warming effect of blood-carrying vessels. The teachings of this invention thus permit and assure that the radiation source is not operated to cause heating of the patient's epidermis until the epidermis has been cooled to the desired depth and temperature, but that firing of the radiation source occurs before there is any significant cooling of the dermis. The invention further permits these controls to be performed completely automatically, thereby reducing the skill level required to safely perform such dermatological procedures, and permitting such procedures to be performed by less skilled and therefore less expensive personnel.

During the firing of the radiation source, control 20 continues to monitor the temperature at sensor 46. If at any time during the firing of the radiation source, there is an increase in temperature at sensor 46 which deviates from what would be anticipated from profile 90, controls 20 can immediately turn off the source 12 to prevent any thermal damage to the patient's epidermis 22.

While for certain treatments, the system of this invention may be able to detect successful completion of the treatment, this is not easy to do, particularly for treatments being performed several millimeters into the dermis. The radiation source is therefore typically fired for a predetermined time interval and/or head 16 is maintained in contact with the patient's skin for a predetermined time interval. Control 20 may determine when such time interval has expired, turn off source 12 when such time period has passed and perhaps generate an audio or visual indication to the operator to remove head 16 from the patient's skim These steps also reduce the skill level required for using the system.

As indicated earlier, one problem with utilizing radiation to treat dermatological conditions is that a significant portion of the radiation applied to the patient's skin is back-scattered and lost, therefore increasing the power required from the radiation source utilized, and thus the cost of the system. One solution to this problem is to efficiently collect radiation back-scattered from the patient's skin and to reflect such radiation back into the patient's skin with minimum loss. FIG. 2 shows a retroreflector which is particularly well suited for performing this function. In particular, waveguide 40 has an aperture which is larger than the optical aperture of the radiation applied to the patient's skin and which is instead substantially equal to the aperture of radiation back-scattered from the patient's skin. Thus, substantially all of the back-scattered radiation is collected in waveguide 40. Waveguide 40 has an external coating or is otherwise designed in manners known in the art so as to totally internally reflect the back-scattered radiation collected therein. Some of such radiation impinges on reflecting surface 74 and is returned through the totally internally reflecting waveguide from such surface to the patient's skin. The remainder of the back-scattered radiation extends into chamber 60 which is also totally internally reflected and ultimately impinges on reflecting surface 76 which returns this radiation with minimal loss to the patient's skin. Thus, the retroreflective design for the head 16 in FIG. 2 results in the collection and retroreflection back into the skin of substantially all back-scattered radiation.

In the discussion above, the side walls and back walls of both waveguide 40 and chamber 60 are fully reflecting so that substantially all of the light retroreflected into waveguide 40 is returned to the patient's skin. However, since radiation entering the waveguide from the skin (before refraction on entering the waveguide), is retroreflected back into the patient's skin at substantially the same angle, such radiation at relatively sharp angles, (i.e., at angles more nearly parallel to the patient's skin than perpendicular) contributes primarily to heating the patient's epidermis, potentially causing thermal damage thereto, without reaching region 30, and therefore without having any therapeutic effect. It is therefore preferable that such sharply angled radiation not be retroreflected or that, as a minimum, the retroreflection of such radiation be substantially attenuated. This can be accomplished in the embodiment of FIG. 2 by for example utilizing an angle dependent coating for the side walls of waveguide 40, the rear wall of waveguide 40, or both so that these walls of the waveguide either do not reflect or minimally reflect large angle radiation entering the waveguide, while more strongly reflecting radiation coming in at a more closely perpendicular angle. Alternatively, the side wall may have varying coefficients of reflection, being less reflective for the portions of the wall closest to the tip or skin contacting surface of waveguide 40 and more reflective toward the rear of the waveguide. Other techniques could also be utilized to assure that waveguide 40 and chamber 60 more strongly reflect retroreflected radiation applied thereto at an angle more nearly perpendicular to the skin surface than radiation applied thereto at an angle more nearly parallel to the skin surface, the perpendicular radiation being substantially fully retroreflected, while the parallel radiation is substantially attenuated.

Figure 4:
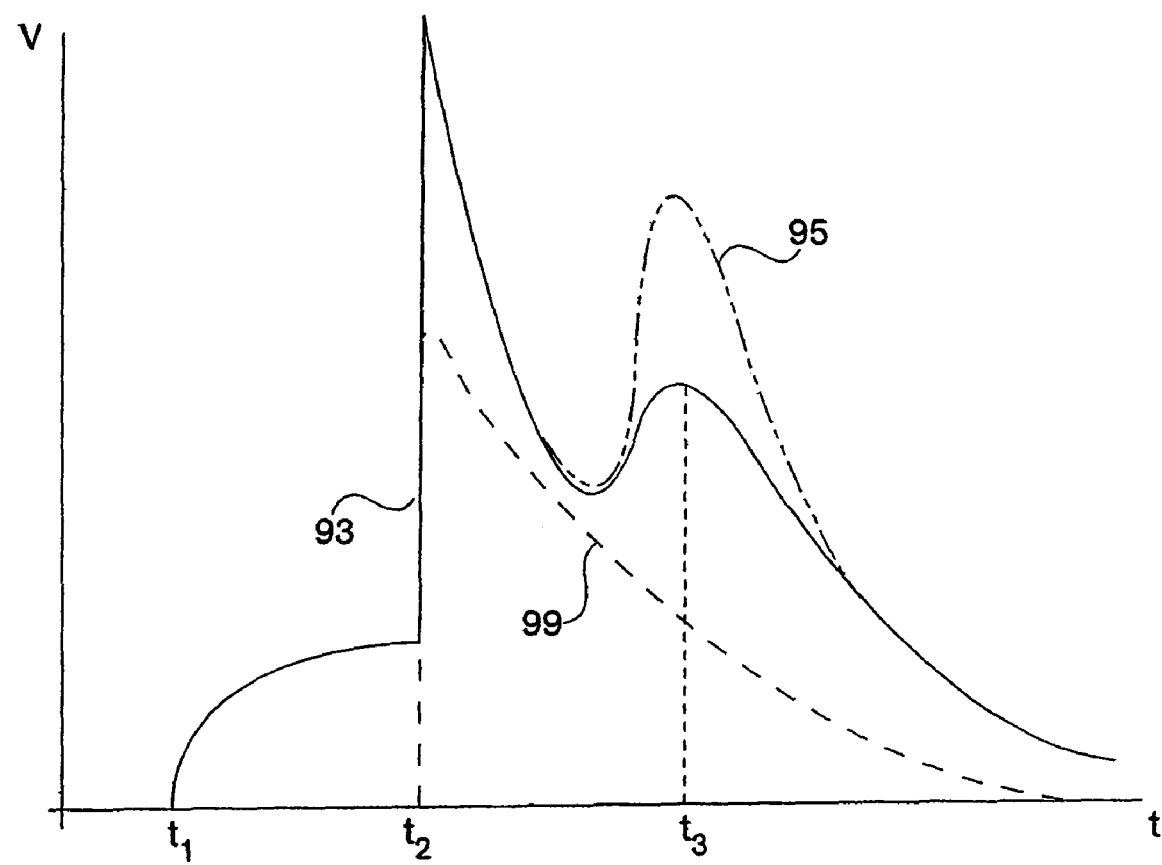
FIG. 4 is a graph illustrating temperature sensor output over time for selected conditions.

FIG. 4 illustrates the voltage output at sensor 46 as a function of time under selected operating conditions. The solid line 93 illustrates a representative output when the waveguide 40 of head 16 is placed in contact with a patient's skin at time $t_1$. From time $t_1$ to time $t_2$ the temperature at the sensor increases as the skin in contact with waveguide 40 is cooled. At time $t_2$, source 12 is operating to apply a radiation pulse through the waveguide to the patient's skin causing an increase in the temperature of the patient's skin which is reflected as a spike in the voltage output from the temperature sensor 46. The temperature then decreases rapidly until just before a time $t_3$ when backskattered radiation from the patient's skin starts to be received in the waveguide. The time between $t_2$ and $t_3$ is a function of the thickness of the patient's epidermis to the DE junction where melanin is being heated and the amplitude of the spike at time $t_3$ is a function the patient's skin type, more energy being reflected for a patient having darker skin, for example spike 95, than for patients having lighter skin. Thus, the amplitude of the spike which occurs at time $t_3$ may be utilized as an indication of the patient's skin type, and this information may be reviewed at least periodically by the system controls, since skin type will vary even for a given patient as different areas of the patient's skin are being treated.

Patient's skin type may also be determined by taking two successive readings, one with head 16 not in contact with the patient's skin and a second with the head in contact with the patient's skin. Curve 93 is an example of the output which is obtained when the head is in contact with the patient's skin, while curve 97 which would start at time $t_2$, is indicative of an output which would be obtained when the laser is fired at time $t_2$ with the head not in contact with the patient's skin. Since the output in air is proportional to the coefficient of absorption for air times the applied laser energy ($V_A=k_0E$) and $V_s$ when the head is in contact with the patient's skin is given by $V_s=k_0E+k_0$ RE, where R is the coefficient of reflection from the patient's skin, $R=(V_s-V_a/k_0E)$. Since $k_0$ and E are known values, the difference in voltage for the two readings provides a reliable indication of the coefficient of reflection from the patient's skin in the area under treatment, or in other words of the patient's skin type. The output from temperature sensor 46 may also be utilized for other purposes.

Figure 5A:
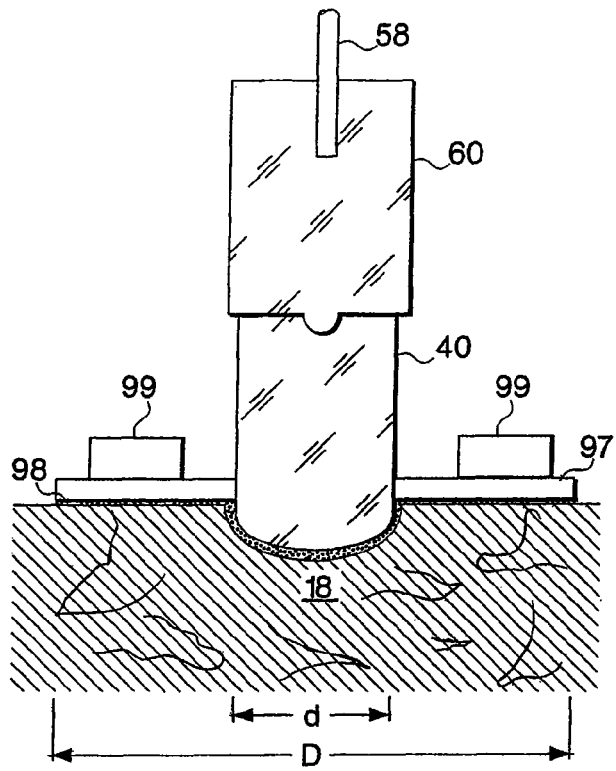
FIGS. 5a and 5b are simplified side sectional views of two alternative heads or applicators for providing a reflection aperture matching the aperture of radiation back-scatter.
Figure 5B:
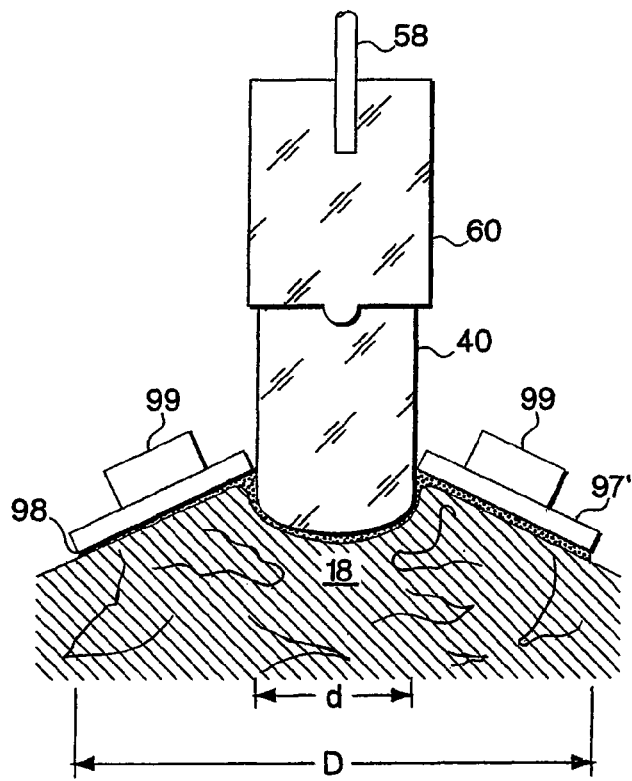

FIG. 5a shows an alternative embodiment of the invention for performing the retroreflector function where the surface area or aperture of waveguide 40 is substantially equal to the optical aperture of radiation applied to the patient's skin. It is therefore smaller than the aperture D of radiation back-scattered from the patient's skin. Therefore, a reflector plate 97 is provided, which may be a specular or diffuse reflector. Plate 97 has a hole which is sized and shaped to permit waveguide 40 to fit therein. Plate 97 may, for example, extend for approximately 1 to 6 millimeters on either side of waveguide 40, but this dimension will vary with application, and can be outside the above range for selected applications. The reflective effect can be enhanced by providing a liquid or other reflective index-matching substance 98 between the skin 18 and the waveguide 40/plate 97, which substance has a reflective index equal or greater than the reflective index of the skin. This decreases the total internal reflection from the skin surface, allowing better return of radiation into the deep layers of skin by reflector 97. Thermoelectric elements 99 in contact with reflective plate 97, which may be formed of a material having good thermal conducting properties such as metal, can be utilized to heat plate 97 to a temperature of, for example, 45-50° C. Plate 97 can thus preheat the area of the patient's skin surrounding the area where radiation is to be applied, thereby increasing the temperature at the treatment area in the dermis, and thus decreasing the light energy required for performing the desired treatment. FIG. 5b illustrates an alternative embodiment wherein the reflector 97' has an enhanced efficiency by being formed in a cone or other concave shape. This results in the back-scattered light reflected into the skin being concentrated in the region of the radiation or collimated beam delivered into the skin through waveguide 40, thus increasing the quantity of radiation delivered to the treatment area.

Except for the shape of the reflection plate 97', the embodiment of FIG. 5b otherwise functions in the same way as the embodiment of FIG. 5a. As for the embodiment of FIG. 2, retroreflection from waveguide 40 can be angle dependent for the embodiments of FIGS. 5a and 5b and, particularly for the embodiment of FIG. 5a, reflection from plate 97 can also be made angle dependent by suitably coating the reflecting surface thereof.

FIGS. 6a and 6b show another embodiment of the invention which differs from those previously described in that reflection plate 97" is even more angled than for the embodiment of FIG. 5 and is generally in the form of a truncated cone which is secured to the lower end of waveguide 40 in a manner so as to form a substantially air-tight seal therewith. Such securing may be by providing a pressure fit between plate 97" and waveguide 40, but is preferably achieved by applying a suitable adhesive between the two components. Another alternative would be to have some form of screw thread formed in or on waveguide 40 which mates with a corresponding tread on plate 97", but such tread might interfere with the optical properties of waveguide 40. A hose 100 passes between plate 97" and waveguide 40 and is sealed there between, hose 100 being attached to a source of negative pressure (for example vacuum pressure) (not shown). As may be best seen in FIG. 6a, when head 16 of this embodiment is pressed against skin 16, a chamber 99 is formed which is defined by the light reflecting walls of plate 97", the lower surface of waveguide 40, and the surface of the patient's skin 18 which is inside the cone of plate 97". Plate 97" will sometimes also be referred to hereinafter as a standoff.

In operation, once head 16 is in the position shown in FIG. 6a, vacuum is applied through hose 100 to chamber 99 to remove air therefrom. This has the effect of drawing a portion or fold 105 of the patient's skin into chamber 99 and into contact with the lower skin-contacting surface of waveguide 40. This can reduce the distance between waveguide 40 and the target volume in skin portion 105 at which treatment is desired and also brings this target volume into chamber 60 where back-scattered radiation retroreflected from the reflecting walls of plate 97" concentrate this radiation on the target volume. This reduces the amount of energy required from EM source 12 and significantly enhances the overall efficiency of the system. The depth of chamber 99 from the bottom of waveguide 40 to the skin surface would typically be in the 5 mm range and should normally not be more than approximately 10 mm. The diameter D of standoff or plate 97" at the skin-contacting end thereof is, as for the embodiment of FIGS. 5a and 5b substantially equal to the aperture of back-scatter radiation.

FIG. 7 shows an embodiment of the invention which differs from that shown in FIG. 6 in that, instead of a vacuum line 100 being utilized to obtain reduced or vacuum pressure in chamber 99, standoff 101 is in the form of a bellows which collapses when head 16 is pressed against the skin as shown in FIG. 7a forcing air out of chamber 99. When pressure on head 16 is removed, or if slight upward pressure is applied to the head, bellows 101 straightens as shown in FIG. 7b. The vacuum in chamber 99 holds bellows 101 against the skin resulting in skin fold 105 again being drawn into chamber 99 as bellows 101 returns to its normal position. The embodiment of FIG. 7 functions substantially the same as the embodiment of FIG. 6 with the inside of bellows 101 having a reflective coating or otherwise being reflective. While the base of bellows or standoff 101 has only a slightly larger aperture than the aperture d of waveguide 40, this is not a problem since substantially all of the back-scattered radiation from the skin is emitted into chamber 99 where it is reflected in a concentrated manner back to the target volume and there should be virtually no back-scattered radiation outside of chamber 99. Sharply angled radiation is also productively utilized for these embodiments. An effect substantially the same as that of FIG. 7 can be achieved by using a standoff in the form of a suction cup in lieu of the standoffs 97" or 101 as shown.

FIGS. 8a-8c show still another embodiment of the invention which differs from that shown in FIG. 7 in that a ring 102 of an elastic material is substituted for the bellows 101. When ring 102 is pressed against the skin as shown in FIG. 8b, the ring deforms permitting waveguide 40 to move substantially into contact with skin 18 as air is forced out of chamber 99. When the pressure is released, elastic ring 102 returns to the condition shown in FIG. 8c, resulting in skin fold 105 being drawn into the chamber as shown.

While three standoff configurations have been shown and/or described above for achieving vacuum pressure, or at least negative pressure, in chamber 99 by collapsing a standoff and then permitting it to return to its normal position, the embodiments shown and/or described are by way of illustration only, and other standoff configurations for achieving the same objective might also be utilized. Further, in addition to the use of vacuum hose 100 as shown in FIG. 6, other methods known in the art may be used for achieving the desired reduced pressure in chambers 99 so as to cause a fold of skin 105 to be drawn therein for irradiation.

Figure 9:
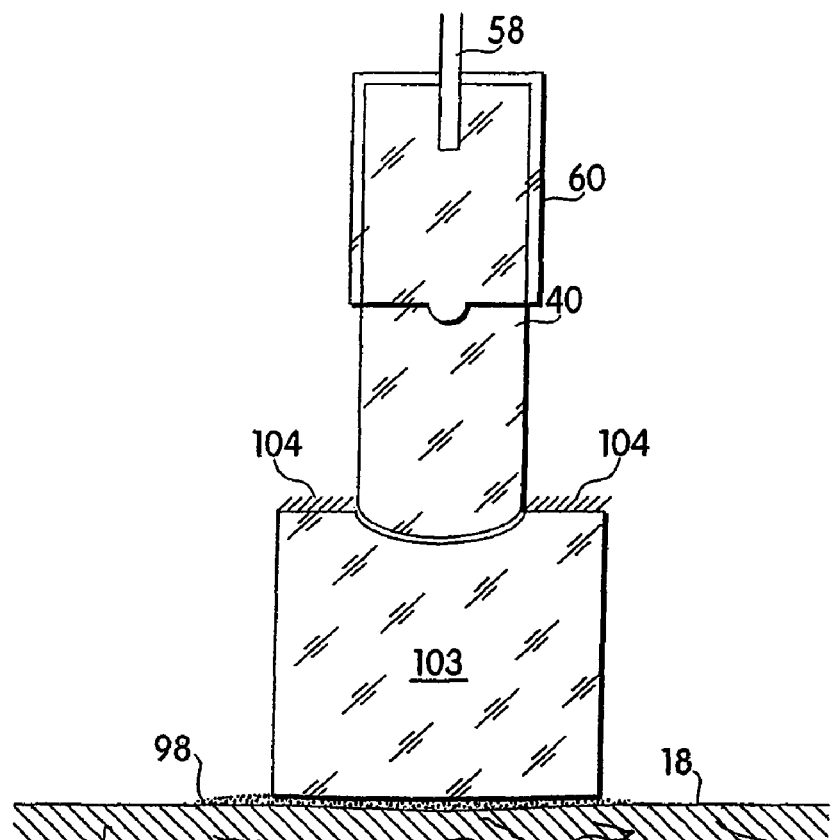
FIG. 9 is a simplified side sectional view of a head for an alternative embodiment of the invention which provides an expanded optical aperture for the head.

FIG. 9 shows still another embodiment of the invention which differs from those previously shown in that, rather than a bottom surface of waveguide 40 being in contact with the patient's skin 18, the lower end of waveguide 40 is in contact with a second waveguide 103 which is preferably of sapphire or other material having good optical and thermal conduction properties. Sapphire is particularly preferred, because it also provides a fairly good optical index match with skin. Index matching material 98 may be utilized between waveguide 103 and the patient's skin to further enhance this match. While not specifically shown in FIG. 9, waveguide 103 would also have, for preferred embodiments, one or more temperature sensors 46 positioned close to its skin-contacting surface and one or more thermoelectric elements 48 or other temperature control elements in contact therewith to preheat and/or cool the patient's skin 18 as required. A reflective coating 104 may also be provided on the rear surface of waveguide 103 to, in conjunction with the retroreflector previously described for waveguide 40, retroreflect substantially all radiation back-scattered from the patient's skin. Angle dependent retroreflection might also be employed for this embodiment using techniques previously discussed, such angle dependent retroreflection occurring at least for waveguide 103, and preferably for both waveguides. The advantage of the embodiment shown in FIG. 9 is that it significantly enlarges the optical aperture for treatment, permitting treatment over a relatively large area, for example hair removal over a patient's legs or back, to be accomplished far more rapidly than when a head having a smaller aperture is utilized. The skin-contacting surface of waveguide 103 may have a variety of shapes, and may for example be circular or square. A circular waveguide 103 might for example have a diameter of approximately 1 inch while a square waveguide 103 might have sides 2 cm long, the height of waveguide 103 preferable being roughly 1.5 times this dimension. These dimensions are, however, being provided by way of illustration only and the specific dimensions of waveguide 103 will vary with application.

Figure 10:
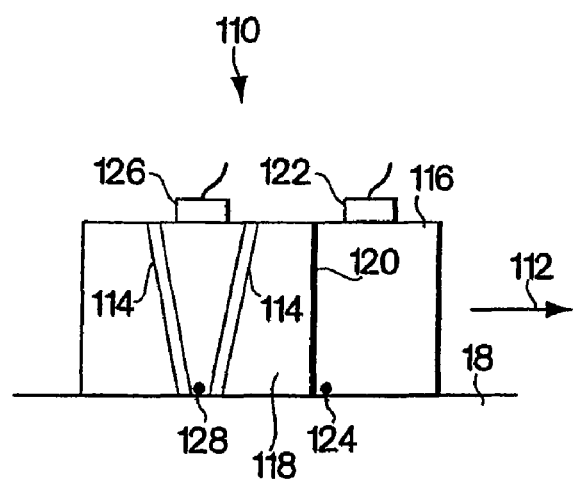
FIG. 10 is a simplified side sectional view of a head for an alternative embodiment which head is suitable for moving across a patient's skin during treatment.

In the discussion to this point, it has been assumed that the head utilized is applied to a point on a patient's skin where treatment is to be performed and that, after a suitable period of time has passed for cooling of the skin to the DE junction to have occurred, an optical radiation pulse, for example a laser pulse, is applied through the waveguide to treatment area 30. FIG. 10 shows an embodiment of the invention which, like the embodiments taught in application Ser. No. 09/078,055, is intended to be in contact with the patient's skin 18 and to be moved in direction 112 over the skin while remaining in contact therewith. Radiation applied to waveguides light paths 114 in this head may be continuous wave or may be pulsed at a high enough rate to permit movement of the head over the treatment area. For the embodiment shown in FIG. 10, the head has an area 116 ahead of waveguides 114 which passes over the treatment area before radiation is applied thereto. Region 116 is preferably of thermally conductive material and is insulated from a second region 118 of the head, which is preferably also of a thermally conductive material, by a thermally insulating layer 120. A thermal electric element or other suitable heater/chiller 122 is in contact with portion 116 and may be used to either preheat or precool the treatment area. For example, if element 122 is a heater, it can heat the skin down to region 30 to a temperature below that at which thermal damage would occur. Further, a temperature sensor 124 is provided, for example up to 5 mm from the skin contacting surface (and preferably less, i.e., to 1 to 2 mm) to indicate skin temperature at for example the DE junction. Sensor 124, by detecting the heating of melanin in the epidermis provides an indication of skin type for the patient, which indication can be used to control the radiation applied. It also assures that overheating in the epidermis does not occur. A thermal electric element or other suitable cooler 126 connected to region 118 cools the epidermis ahead of waveguides 114 coming over a treatment area. A temperature sensor 128 can also be provided in region 118, for example up to 5 mm from the skin contacting surface, to assure that this region has cooled sufficiently before radiation is applied thereto and to protect against thermal damage to this region. While a single pair of waveguides 114 are shown in FIG. 10, typically a plurality of such waveguides would be stacked adjacent to each other in a direction into the figure. Two or more heaters/chillers 122, 126 could also be provided and two or more sensors 124, 128 could also be provided. Further, the sensor technology of this invention could also be utilized with other ones of the embodiments shown in application Ser. No. 09/078,055.

While the invention has been described above with reference to a particular system 10 and to particular head designs 16, neither are limitations on the invention. In particular, other techniques known in the art, for example circulating water or air, could be utilized for cooling waveguide 40 in lieu of thermoelectronic cooling elements 48, although such thermoelectronic cooling elements are at this time preferred. Some elements 48 (or other thermal control elements) might also be used to heat waveguide 40 to preheat the target area, after which either the same or different thermal control elements would be used to cool the waveguide as previously indicated to cool the patient's epidermis in the treatment area. A lens may also be substituted for waveguide 40, although waveguide 40 is currently preferred because of its superior thermal properties and its superior performance in retroreflection.

What is claimed is:

1. A dermatological system, comprising:
   an optical waveguide for transmitting radiation received at a first end thereof to a second end configured to directly contact a subject's skin surface so as to irradiate a portion of the skin, and
   a reflecting plate adapted to contact a portion of the skin surface and surrounding at least a portion of said second waveguide end,
   said reflecting plate returning at least a portion of radiation backscattered from the irradiated skin portion to the subject's skin.

2. A dermatological system according to claim 1, wherein said plate comprises an aperture sized and shaped for receiving at least a portion of said second end of the waveguide.

3. A dermatological system according to claim 1, wherein said reflecting plate has a concave shape.

4. A dermatological system according to claim 1, wherein said reflecting plate is formed of a thermally conductive material.

5. A dermatological system according to claim 4, further comprising a heating element in thermal contact with said reflecting plate for heating thereof.

6. A dermatological system according to claim 5, wherein said heating element comprises a thermoelectric element.

7. A dermatological system according to claim 1, wherein said reflective plate comprises an angle-dependent reflective coating.

8. A dermatological system according to claim 1, wherein said reflective plate provides specular reflection of radiation.

9. A dermatological system according to claim 1, wherein said reflective plate provides diffuse reflection of radiation.

10. A dermatological system according to claim 1, wherein said second end of the waveguide comprises reflecting side walls for returning at least a portion of radiation applied to the patient's skin that is retroreflected into the waveguide back to the patient's skin.

11. A dermatological system according to claim 10, wherein said waveguide further comprises a chamber optically coupled to the second end for internally reflecting at least a portion of backscattered radiation extending through the second end into said chamber back to the patient's skin.

12. A system for treating a dermatological condition located in a volume of a patient's skin, comprising:
    a solid optical waveguide having a first end for receiving radiation generated by a radiation source and a second end configured to directly contact a patient's skin, said waveguide transmitting said received radiation from the first end to the second end for application to the patient's skin, and
    a reflector disposed within said waveguide for returning at least a portion of backscattered radiation entering the waveguide back to the patient's skin, and
    a chamber optically coupled to the first end of the waveguide for internally reflecting at least a portion of backscattered radiation extending through the second end of the waveguide into said chamber back to the patient's skin.

13. A system according to claim 12, wherein said reflector comprises reflecting side walls of said waveguide, said reflecting walls returning at least a portion of radiation applied to the patient's skin that is retroreflected into the waveguide back to the patient's skin.

14. A system according to claim 12, wherein said second end of the waveguide has an aperture at least substantially as large as a backscatter aperture of radiation backscattered from the patient's skin.

15. A system according to claim 14, wherein said reflector has a reflection aperture D at least substantially as great as said backscatter aperture.

16. A system according to claim 12, wherein said reflector comprises at least a portion of said second end of the waveguide formed as a reflection plate.

17. A system according to claim 12, wherein said reflection plate has a concave shape.

18. A system according to claim 12, wherein said reflector comprises a portion disposed along at least a portion of a sidewall of said waveguide.

19. A system according to claim 18, wherein said reflector has a coefficient of reflection for reflecting backscattered radiation more strongly at angles nearly perpendicular to the skin surface than at angles parallel to the skin surface.

20. A system according to claim 12, wherein said solid waveguide is formed of a thermally conductive material.

21. A system according to claim 12, wherein said solid waveguide comprises sapphire.

* * * * *